(12) United States Patent
Lawandy

(10) Patent No.: US 10,379,114 B2
(45) Date of Patent: *Aug. 13, 2019

(54) NONDEGENERATE TWO-WAVE MIXING FOR IDENTIFYING AND SEPARATING MACROMOLECULES

(71) Applicant: Solaris Nanosciences, Inc., Providence, RI (US)

(72) Inventor: Nabil Lawandy, Saunderstown, RI (US)

(73) Assignee: Solaris Nanosciences, Inc., Providence, RI (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/729,408

(22) Filed: Oct. 10, 2017

(65) Prior Publication Data

US 2018/0106794 A1 Apr. 19, 2018

Related U.S. Application Data

(63) Continuation-in-part of application No. 15/242,345, filed on Aug. 19, 2016, now Pat. No. 9,970,854.

(Continued)

(51) Int. Cl.
*G01N 15/02* (2006.01)
*G01N 33/543* (2006.01)
(Continued)

(52) U.S. Cl.
CPC ... *G01N 33/54346* (2013.01); *G01N 15/0205* (2013.01); *G01N 15/14* (2013.01);
(Continued)

(58) Field of Classification Search
CPC ....... G01N 15/0205; G01N 2015/0065; G01N 27/44721; C08J 3/203; C08K 5/098; C08K 5/20; C08K 5/523; C08L 23/12
(Continued)

(56) References Cited

U.S. PATENT DOCUMENTS 5,094,532 A  3/1992 Trainer et al.
6,219,138 B1  4/2001 Swanson et al.
(Continued)

OTHER PUBLICATIONS

Written Opinion of the International Searching Authority in PCT/US2017/055941 (dated Jan. 5, 2018).
(Continued)

*Primary Examiner* — Isiaka O Akanbi
(74) *Attorney, Agent, or Firm* — Pryor Cashman LLP

(57) ABSTRACT

A method for determining a radius of elements suspended in a medium includes binding the elements to nanoparticles to form bound element-nanoparticle aggregates, superposing first and second Doppler-shifted optical waves having a variable frequency shift between them in the medium such that there is a gain in energy of the first optical wave with respect to the second optical wave, varying the frequency shift and measuring the gain while varying the frequency shift to determine the value of the frequency shift at which there is a peak in the gain, determining the radius of the bound element-nanoparticle aggregates based on the value of the frequency shift at which there is a peak in the gain, and determining the radius of the elements based on the radius of the bound element-nanoparticle aggregates.

32 Claims, 37 Drawing Sheets

Related U.S. Application Data

(60) Provisional application No. 62/207,168, filed on Aug. 19, 2015, provisional application No. 62/406,268, filed on Oct. 10, 2016, provisional application No. 62/489,302, filed on Apr. 24, 2017.

(51) Int. Cl.
*G01N 15/14* (2006.01)
*G01N 33/553* (2006.01)
*G01N 33/545* (2006.01)
*G01N 15/10* (2006.01)
*G01N 15/00* (2006.01)

(52) U.S. Cl.
CPC ..... *G01N 33/545* (2013.01); *G01N 33/54353* (2013.01); *G01N 33/553* (2013.01); *G01N 2015/0038* (2013.01); *G01N 2015/0053* (2013.01); *G01N 2015/0065* (2013.01); *G01N 2015/1006* (2013.01); *G01N 2015/1087* (2013.01); *G01N 2015/1454* (2013.01)

(58) Field of Classification Search
USPC .......................................... 356/336–338, 484
See application file for complete search history.

(56) References Cited

U.S. PATENT DOCUMENTS

| | | | |
|---|---|---|---|
| 6,281,973 | B1 | 8/2001 | Trainer |
| 2011/0210002 | A1 | 9/2011 | Hsieh et al. |
| 2012/0044493 | A1* | 2/2012 | Smart ................ G01N 15/0211 356/336 |
| 2012/0055264 | A1* | 3/2012 | Sinha ...................... G01F 1/663 73/861.25 |
| 2015/0276571 | A1* | 10/2015 | Hajjarian ............... G01N 21/41 73/54.02 |

OTHER PUBLICATIONS

International Search Report in PCT/US2017/055941 (dated Jan. 5, 2018).

Adler et al., "Viscosity of picoliter volumes measured by nondegenerate two-wave mixing," Optics Communications 81 (1-2):1-18 (Feb. 1, 1991).

* cited by examiner

Time (1 ms/div.)

Time (2 ms/div.)

L1 and L2 -F=6.2 mm, NA=0.30 Aspheric Lens, AR 300-700 mm

- Mixture of proteins X,Y, Z, G
- Binding selective for X $a_H$ = Hydrodynamic Radius $a_T$ = TEM measured radius = 25nm for Au

- Protein-A bound to 50nm diameter Au
- Increase in the hydrodynamic radius of 8.3 nm

- Protein-A bound to 50nm diameter Au coated with PVP
- Increase in the hydrodynamic radius of <u>2.8nm</u>

- 135 Protein-A molecules on a 50nm Au nanoparticles

- 50 Protein-A coated Au nanoparticles have been measured $10^{-20}$ Moles of Protein-A
Or
10 Zeptomoles !

$$\alpha_{comp} = \left[\frac{\varepsilon_{PVP}\varepsilon_a - \varepsilon_m\varepsilon_b}{\varepsilon_{PVP}\varepsilon_a + 2\varepsilon_m\varepsilon_b}\right](r_2^3)$$

$\varepsilon_b = \varepsilon_{Au}P + \varepsilon_{PVP}(3 - P)$ $\varepsilon_a = \varepsilon_{Au}(3 - 2P) + 2\varepsilon_{PVP}P$ $P = 1 - \left(\dfrac{r_1}{r_2}\right)^3$

NONDEGENERATE TWO-WAVE MIXING FOR IDENTIFYING AND SEPARATING MACROMOLECULES

CROSS-REFERENCE TO RELATED APPLICATIONS

The present application is a continuation-in-part of U.S. patent application Ser. No. 15/242,345, filed Aug. 19, 2016, now pending, which claims priority to U.S. Provisional Patent Application No. 62/207,168, filed Aug. 19, 2015. The present application claims priority to U.S. Provisional Patent Application Nos. 62/406,268, filed Oct. 10, 2016, and 62/489,302, filed Apr. 24, 2017. The disclosures and teachings of the aforementioned applications are incorporated herein by reference.

TECHNICAL FIELD

The present invention involves using nondegenerate two-wave mixing in colloidal suspensions to identify and separate macromolecules, particularly biomolecules such as proteins, antibodies, DNA strands, red blood cells and semen, and molecular and biological moieties.

BACKGROUND OF THE INVENTION

Biomolecules such as proteins, antibodies, DNA strands, red blood cells and semen, molecular and biological moieties, and large molecules in general, are commonly detected and separated using electrophoresis in gels and other media. Electrophoresis is the motion of dispersed particles relative to a fluid under the influence of a spatially uniform electric field. This electrokinetic phenomenon was observed for the first time in 1807 by Ferdinand Frederic Reuss (Moscow State University), who noticed that the application of a constant electric field caused clay particles dispersed in water to migrate. Electrophoresis is ultimately caused by the presence of a charged interface between the particle surface and the surrounding fluid, and it is the basis for a number of analytical techniques used in biochemistry for separating molecules by size, charge or binding affinity.

Electrophoresis is a technique used in laboratories to separate macromolecules based on their size. The technique involves applying a negative charge so that particles such as proteins move toward a positive charge. This technique is used for both DNA and RNA analysis. Polyacrylamide gel electrophoresis (PAGE) has a clearer resolution than electrophoresis based in agarose and is more suitable for quantitative analysis. Using PAGE, DNA foot-printing can identify how proteins bind to DNA. PAGE can be used to separate proteins by size, density and purity, and further may be used for plasmid analysis for developing an understanding of bacteria becoming resistant to antibiotics.

Recently, dielectrophoresis (DEP), which uses electric field gradients, has been utilized for similar applications and cell separation. DEP does not require that the macromolecules be charged, and instead relies on the polarizability of the macromolecules. Dielectrophoresis occurs when a polarizable particle is suspended in a non-uniform electric field. The electric field polarizes the particles, and the particles' poles experience a force along the field lines, which force can be either attractive or repulsive, according to the orientation of the dipole. Since the field is non-uniform, the pole experiencing the greater electric field will dominate the other, and the particle will move. The orientation of the dipole is dependent on the relative polarizability of the particle and medium, in accordance with Maxwell-Wagner-Sillars polarization. Further, since the direction of the force is dependent on field gradient rather than field direction, dielectrophoresis will occur in alternating current as well as direct current electric fields; polarization, and hence the direction of the force, will depend on the relative polarizabilities of particle and medium. If the particle moves in the direction of increasing electric field, the behavior is referred to as positive DEP. If acting to move the particle away from high field regions, it is known as negative DEP (nDEP). As the relative polarizabilities of the particle and medium are frequency dependent, varying the energizing signal and measuring the manner in which the force changes can be used to determine the electrical properties of particles; this allows for the elimination of electrophoretic motion of particles due to inherent particle charge.

Additional phenomena associated with dielectrophoresis are electrorotation and traveling wave dielectrophoresis (TWDEP). These require complex signal generation equipment and patterned electrode structures to create the required rotating or traveling electric fields; as a result of this complexity, these techniques have found less favor than conventional dielectrophoresis among researchers.

In addition to electrophoretic separation, identification and separation is accomplished by methods of attaching proteins or molecule-specific fluorescent or chemiluminescent markers used in the Southern Blot and Western Blot assays to identify electrophoretically separated macromolecules obtained from the lycing of cells. The techniques of electrophoresis and blotting are capable of handling biological moieties ranging from 10-1000 kD, or 3-100 nanometers along various dimensions. While electrophoresis and blotting technologies are expected to constitute a $2 billion market by 2020, there are several shortcomings associated with these technologies, including a one-day performance cycle duration, being limited to charged species, difficulty handling large molecules (e.g., titin), a requirement of milliliter samples and several reagents, and an inability to produce information regarding dielectric properties. More recently, nonlinear four-wave mixing techniques have been employed to identify specific molecules in conjunction with electrophoretic or dielectrophoretic separation. For example, ultrasensitive detection of proteins and antibodies by absorption-based laser wave-mixing detection using a chromophore label has been demonstrated by Tong et al. The four-wave mixing signal results in an absorption grating formed by the linkage of a non-fluorescing chromophore label, Coomassie Brilliant Blue (CBB), which absorbs the laser radiation.

Moreover, dynamic light scattering (DLS) is another approach for determining the size distribution profile of particles in suspension or polymers in solution. See Lim et al., Nanoscale Research Letters 8:381 (2013). This technology is expected to constitute a $200 million market by 2020, but suffers many of the same problems as electrophoresis and blotting, with shortcomings including a requirement of microliter samples, being limited by low level signals, and an inability to produce information regarding dielectric properties. Further, this technology produces large errors outside a narrow size range.

In light of these deficiencies associated with electrophoresis/blotting and DLS, particularly the requirement for large amounts of material in order to perform these processes as well as the large errors, e.g., up to 500%, produced based on concentration, there exists a need for superior means of identifying and separating macromolecules.

SUMMARY OF THE INVENTION

The method and apparatus of the present invention is directed to the identification and separation of macromolecules based on the nonlinear optical effect of nondegenerate two-wave mixing and, in particular, the forces resulting from the application of radiation pressure on particles in a colloidal suspension due to the interference of optical waves. The use of nondegenerate two-wave mixing in colloidal suspensions to measure the viscosity of liquids is described in C. L. Adler and N. M. Lawandy, "Viscosity of picoliter volumes measured by nondegenerate two-wave mixing," Optics Communications, Vol. 81, No. 1,2 (Feb. 1, 1991).

The method and apparatus of the present invention includes using ultra low power or low intensity radiation in which two light beams having frequencies differing by about tens of Hertz to 10 MHz are interfered in a colloidal suspension sample to produce a moving optical light intensity grating at controllable velocities from 0 to 10 m/s. The optical intensity grating interacts with the non-absorbing macromolecules and moves them against the drag of the solvent of the suspension, which in most biological applications is primarily water. By varying the frequency difference between the two beams, an exchange of energy between the two beams occurs, which has a peak at a value of the frequency difference that depends on the diffusion coefficient of the macromolecule. The diffusion coefficient is a function of the "size" and mass of the macromolecule, its shape, and the viscosity of the liquid or host.

The method and apparatus of the present invention can be used with a macromolecule-specific antibody or linking mass to identify or determine a specific molecule through selective binding, namely by changing the molecule's size and shape and shifting the frequency peak to a new value, i.e., performing an assay. In addition, the use of frequency-shifted and polarization-rotating polarized light can be used to determine ellipticity, i.e., rod-to-sphere limit, of the molecules being dragged by the grating to perform a second level of identification or separation.

The goal of the invention is to provide an optical technique that is accurate and not difficult to perform to replace or complement electrophoresis, blotting and detection for analyzing macromolecules, such biomolecules, in a colloidal suspension. Such a technique would require only minutes, rather than days in the case of electrophoresis, to perform, and can be used to analyze molecules having sizes on the order of gigaDaltons and in solutions of volumes on the order of picoliters, thus involving small quantities of lysate and reagents when analyzing biomolecules. In addition, the ability to use light that is not absorbed by the macromolecular moieties and to focus on spot sizes of a few microns provides the invention with the potential to be used in living cells, either in vitro or in vivo, and by catheter born probes.

In general, in one aspect, the invention features a method for determining a radius of elements suspended in a medium, including binding the elements to nanoparticles to form bound element-nanoparticle aggregates, superposing first and second Doppler-shifted optical waves having a variable frequency shift between them in the medium such that there is a gain in energy of the first optical wave with respect to the second optical wave, varying the frequency shift and measuring the gain while varying the frequency shift to determine the value of the frequency shift at which there is a peak in the gain, determining the radius of the bound element-nanoparticle aggregates based on the value of the frequency shift at which there is a peak in the gain, and determining the radius of the elements based on the radius of the bound element-nanoparticle aggregates.

Implementations of the invention may include one or more of the following features. The first and second optical waves may have low intensities. The radius of the bound element-nanoparticle aggregates may be a hydrodynamic radius that is inversely related to the value of the frequency shift at which there is a peak in the gain. The elements may be bioparticles, which may be proteins, antibodies, DNA strands, red blood cells, semen, or molecular or biological moieties. The nanoparticles may be gold nanoparticles. The nanoparticles may be coated nanoparticles, and the coating of the coated nanoparticles may include polyvinylpyrrolidone. The elements may be bound to the nanoparticles via linkers, which may be thiols or amines. The phase shift may vary from about 10 Hz to 10 MHz. The method may further include varying the conditions of the medium to analyze a conformation of the bound element-nanoparticle aggregates, and the conditions varied may be temperature or pH or both. The optical waves may be light beams or laser beams. The first and second optical waves may be substantially not absorbed by the bound element-nanoparticle aggregates or the medium. The bound element-nanoparticle aggregates may be anisotropically shaped and the first and second optical waves have a linear polarization, and the method further including rotating the linear polarization of the first and second optical waves at an annular frequency and varying the annular frequency to induce a torque on the bound element-nanoparticle aggregates to determine the anisotropy of the bound element-nanoparticle aggregates. Determining the anisotropy of the bound element-nanoparticle aggregates may provide an indication of the hydrodynamic molecular shape of the bound element-nanoparticle aggregates. The bound element-nanoparticle aggregates may be anisotropically shaped, and the method further including applying an electric field to the medium to align the bound element-nanoparticle aggregates in a direction. The elements may be selectively bound to the nanoparticles.

The presently-described invention presents a new method of characterizing molecules with 1 nanometer resolution, which is $10^9$ smaller than with electrophoresis and $10^6$ smaller than with DLS. The method relies on optical forces and flows, not random motion and weak light scattering, which permits analysis of large concentration ranges without error. The method can be utilized with both charged and neutral molecules. Moreover, changes in diameter associated with zeptomole quantities have been demonstrated as assays, and changes with ionic environment inherent in gel methodologies can be detected. Finally, dielectric properties and associated information can be obtained simultaneously with the invention.

DETAILED DESCRIPTION OF THE PREFERRED EMBODIMENTS

The technique of the present invention and the systems to which it is applied involve the use of solvents containing colloidal suspensions of macroparticles, which may be bioparticles such as proteins, antibodies, DNA strands, red blood cells and semen, and molecular and biological moieties. In its operation, the present invention involves the use of two optical waves, such as beams of laser light, interfering with each other to create a traveling intensity grating in the colloidal suspension of particles. The optical waves are selected so that they substantially are not absorbed by and do not heat the suspension or the particles suspended in it.

Figure 1A:
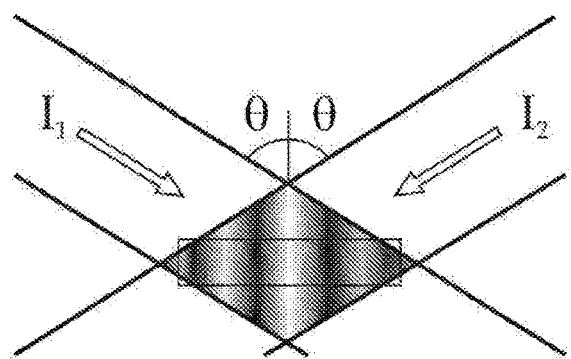
FIG. 1A illustrates the intensities of two interfering optical waves.
Figure 1B:
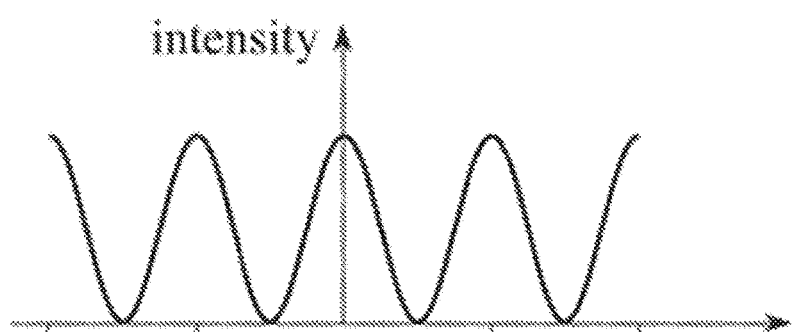
FIG. 1B illustrates a standing wave intensity grating pattern formed by the two interfering optical waves of FIG. 1A.

As illustrated in FIG. 1A, the intensities of two optical waves represented by $I_1$ and $I_2$, both at an angle $\theta$ to a normal, create an intensity grating pattern in the form of a standing wave as illustrated in FIG. 1B. The total intensity of the interfering optical waves may be represented as follows:

$$\langle |E_{total}(P, t)|^2 \rangle_{time\ avg.} = \frac{a_1^2(P)}{2} + \frac{a_2^2(P)}{2} + a_1(P)a_2(P)\cos(\phi_1(P) - \phi_2(P))$$

The total intensity is then (in *MKS* units), $$I_{total}(P) \equiv \varepsilon_0 c \langle |E_{total}(P, t)|^2 \rangle_{time\ average}\ (W/m^2)$$

$$= \varepsilon_0 c \frac{a_1^2(P)}{2} + \varepsilon_0 c \frac{a_2^2(P)}{2} + \varepsilon_0 c a_1(P)a_2(P)\cos(\phi_1(P) - \phi_2(P))$$

$$= I_1(P) + I_2(P) + 2\sqrt{I_1(P) \cdot I_2(P)}\ \cos(\phi_1(P) - \phi_2(P)).$$

In the case of identical optical waves having intensity I and differing only in phase, the total intensity $I_{total}$ reduces to the representation $I_{total} = 2I + 2I \cos((4\pi/\lambda)x)$.

Figure 2:
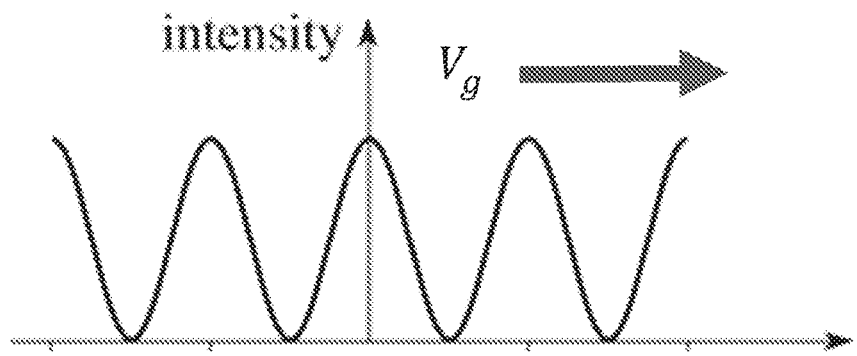
FIG. 2 illustrates a traveling intensity grating pattern formed by two interfering optical waves having a small difference in frequency.

When two optical waves of frequency $\omega$, such as beams emanating from focused low-power solid-state lasers, have a slight difference in their frequency $\delta\omega$, the intensity grating pattern moves at a speed $V_g$, as illustrated in FIG. 2, according to the following relation:

$$V_g = \frac{\delta\omega}{2\omega}c$$

The frequency shift $\delta\omega$ is directly proportional to the speed $V_g$, since rearranging the equation provides that $\delta\omega=2\omega V_g/c$.

When a dielectric particle is placed in an electric field, it develops an induced dipole moment, which in turn interacts with the field itself to lower the energy of the particle. The force F felt by a dipole in an electric field, once oriented, is given by:

$$F = \mu \frac{\partial E}{\partial x}$$

If the dipole is induced by the same electric field having the polarizability $\alpha$, then $\mu=aE$, and the energy of the particle is related to the magnitude of the electric field E, where $\langle E^2 \rangle$ is proportional to the local intensity of the light, as follows:

$$\text{Energy} = -1/2\alpha\langle E^2\rangle \text{ where } \alpha = 4\pi\frac{n^2-1}{n^2+2}a^3 (MKSA \text{ units})$$

where a is the hydrodynamic radius

This results in a time-averaged force $F_g$ on the particle given by $$\langle F_g\rangle = (1/4)\varepsilon_0\varepsilon_h \text{Re}(\alpha)\nabla|E^2|$$

Figure 3:
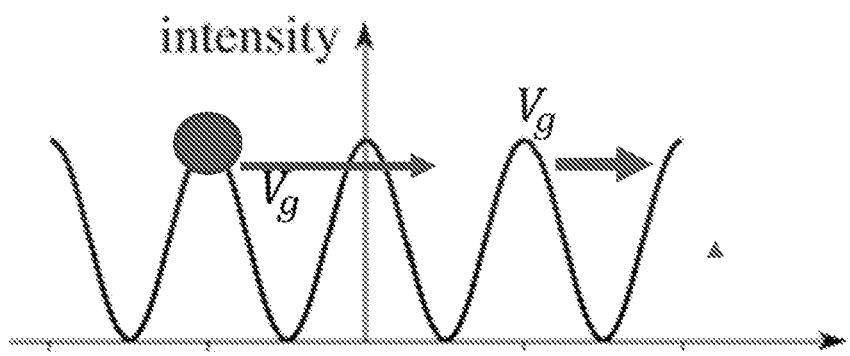
FIG. 3 illustrates particles in high intensity of interfering waves with no frictive forces.

If there were no frictive forces acting on the particle's movement in the solution, the particle would remain in regions of high intensity of interfering waves, as illustrated in FIG. 3. Newton's equations of motions would be satisfied when the particle is on one of the peaks of the intensity grating of the interfering waves and remains at that peak by moving at the same velocity as the grating in the case of two waves with a difference in frequency.

Figure 4:
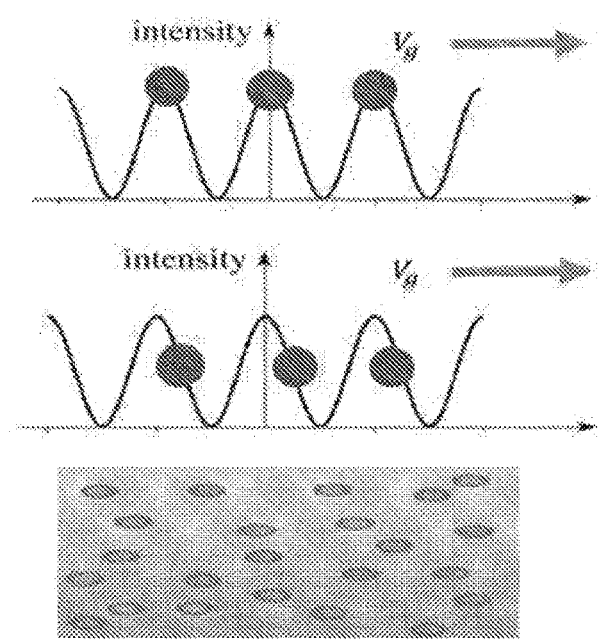
FIG. 4 illustrates particles following the intensity grating of interfering waves with friction.

In a real solution such as water, the particle experiences friction or drag proportional to the viscosity of the liquid and the radius of the particle. Stoke's Law provides a quantification of the drag force $F_d$ as the particle travels through a fluid as $F_d=6\pi r\eta v$, where r is the radius of a sphere representing the particle, $\eta$ is the viscosity of the fluid, and v is the speed of the sphere. The friction or drag causes the particle to follow the intensity grating of the interfering optical waves, as shown in FIG. 4. If the intensity grating moves very slowly, the particles will follow the intensity grating at its peaks. If the intensity grating moves too quickly, the particles will not follow the intensity grating and on average will not move along with the intensity grating. When there are many particles, the particles arrange themselves in a particle grating and move along with the intensity grating if they are able to do so. In particular, at slow grating speeds having a small frequency shift between the interfering optical waves, the particles form a particle grating that is aligned with the moving intensity maxima. At intermediate grating speeds, the particles are trapped in high intensity regions and move with the intensity grating to form a particle grating that moves along with the intensity grating, but is displaced from the intensity peaks; i.e., the particle grating is out of phase with the intensity grating. At high grating speeds, the particles cannot follow the intensity grating at all, and no particle grating is formed.

In a nonlinear colloidal system including particles as described herein, when two counter-propagating Doppler-shifted light beams are superposed in the medium, the traveling intensity grating that results leads to a traveling index grating, which in turn leads to the scattering of one light beam in the direction of the other, i.e., one beam will gain energy at the expense of the other one. When the intensity grating is out of phase with the particle grating, the optical waves forming the gratings exchange energy, with the higher frequency wave gaining energy at the expense of the lower frequency wave. There will be a maximum of energy exchange between the two waves when the particle grating moves with a lag of $\pi/2$ with respect to the intensity grating. An intensity grating moving too fast, i.e. having a large frequency shift, results in the particles not forming a particle grating at all, and an intensity grating moving too slowly results in a particle grating that follows the peaks of the intensity grating.

For low intensity optical waves, the gain G referenced above, namely a measure of the gain of energy by one optical beam at the expense of the other, as well as the amplitude B of the out-of-phase particle grating is given by $$G \sim \frac{\delta\omega\tau}{1+(\delta\omega\tau)^2} \text{ where } 1/\tau = 4k^2 D, k = 2\pi/\lambda \text{ and } D = k_B T/6\pi\eta a$$

$$B = \frac{U(I)}{kT}[G]$$

with a being the hydrodynamic radius of the particles in the colloidal suspension, D being the diffusion coefficient of the particles in the medium, $\lambda$ being the wavelength of the incident optical waves, $k_B$ being Boltzman's constant, and T being the absolute temperature in Kelvin. The Einstein-Stokes relation between diffusion coefficient and viscous drag provides the inverse relationship between the diffusion coefficient D and the molecule's radius a. The amplitude B depends on the relaxation rate $(1/\tau)$ of the grating, with the relaxation rate being determined by the spacing of the grating and the hydrodynamic radius a of the particle.

At low intensities, the peak gain occurs at $\delta\omega=1/\tau$. Thus, by analyzing the two-wave mixing gain as a function of Doppler shift, to determine the $\delta\omega$ at which the maximum relative gain occurs, the hydrodynamic radius of the particles in the suspension can be determined. In particular, $$\delta\omega = \frac{8\pi k_B T}{3\lambda^2 \eta a}$$

and since $\lambda$, T and $\eta$ are known for a particular sample of the suspension under specified conditions, the hydrodynamic radius of the particle can be determined accurately for a particular detected Doppler phase shift $\delta\omega$. By experimentally determining the peak frequency shift, the average size, and accordingly the mass, of a biomolecule in the colloidal suspension can be determined. In particular, the mass of the particle can be estimated by mass=$\rho\pi d^3/6$, where $\rho$ is density and the diameter d of the particle is estimated by the hydrodynamic radius a. Thus, knowing the wavelength of the interfering optical waves and the viscosity of the solvent, the particle's average size, i.e., its hydrodynamic radius and estimated mass can be determined from the peak frequency shift.

The technique described herein is applied to colloidal suspensions including biomolecules such as proteins, antibodies, DNA strands, red blood cells and semen, and molecular moieties. It has previously been shown that using optical waves with a frequency of 5 KHz, spheres having an average sizes of 109 nm, which have a mass in the gigaDalton range, could be detected and measured. The present invention may be applied to systems in which optical waves with a frequency difference of 1 MHz detect and measure particles with a sphere radius of 1 to 5 nm and masses as small as a few thousand Daltons, e.g., 30 kiloDaltons. In the case of a polystyrene sphere of diameter 0.09 micron, which has a mass of $4.0 \times 10^{-16}$ gram or 240,000 kiloDaltons, the frequency at which the maximum exchange of energy between the two beams occurs at approximately 3200 Hz and corresponds to the peak in the curve of the nondegenerate two-wave mixing gain curve shown in FIG. 8. For example, for a spherical molecule or biological moiety with a radius of 1.5 nm, the expected frequency difference peak is at 288 kHz, with such a macromolecule in a spherical conformation having a mass of approximately 270 kiloDaltons.

Figure 5:
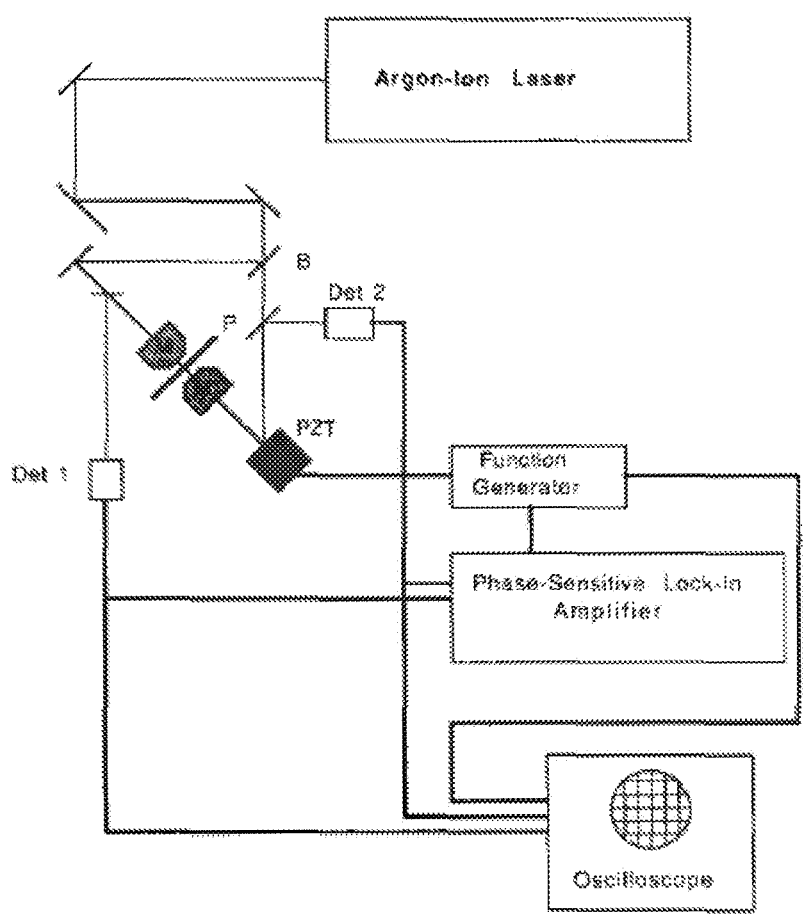
FIG. 5 illustrates an experimental setup for the present invention.

FIG. 5 shows an experimental setup for analyzing a volume of solvent according to the present invention. A mirror moving on a piezoelectric stage driven by a wave signal, e.g., a triangular wave, is used to Doppler-shift the frequency of one of the interfering waves by a small amount to create the moving intensity grating. Other means can be used to create the frequency shift, including electro-optic modulation in materials such as lithium niobate. In addition, nonlinear third order media can also be used where the frequency shift is created by varying an applied quasi-state electric field, the application of a laser pulse, or by varying the intensity of one of the two interfering waves in time as they propagate through the nonlinear medium.

In the example of FIG. 5, an optical wave in the form of a laser light beam is generated using a Laser, which may be a 5 W argon-ion laser running at 514.5 nm. The laser light beam is split into two separate laser beams using a 50/50 beamsplitter B. The second separated laser beam is reflected off a mirror mounted on a piezoelectric transducer PZT to create a controlled, variable frequency shift between the two split laser beams. The interfering beams are directed at sample P. The piezoelectric transducer is driven by a Function Generator. Phase sensitive detection at the piezoelectric transducer displacement frequency insures that only gain antisymmetric in the beam Doppler shift is detected. Piezoelectric transducer displacement may be calibrated using Michelson interferometry. Through reflection, the gain or loss of the first beam, as measured by a detected voltage, is detected by detector Det2. Similarly, the gain or loss of the second beam is detected by detector Det1.

Figure 6:
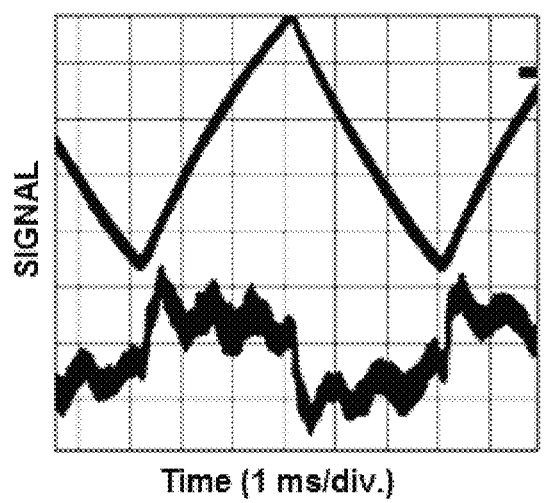
FIG. 6 shows a scope trace of displacement according to triangle wave signal and a nondegenerate two-wave mixing gain signal according to the present invention.

As shown in FIG. 6, in one embodiment, the function generator produces a triangle wave signal to displace the piezoelectric transducer and attached mirror, e.g., at 200 Hz. In the case of a triangle wave signal, the instantaneous speed of the movement of the piezoelectric transducer and mirror is the time derivative or slope of the triangle wave signal, which is constant (except at the inflection points). The speed of movement of the piezoelectric transducer is directly proportional to the voltage applied to the piezoelectric transducer, according to the relation $v_{pzt}=C_{pzt}Vf$, where $v_{pzt}$ is the speed, $C_{pzt}$ is a constant associated with the piezoelectric transducer, e.g., 2.7 microns/volt, V is the voltage applied to the piezoelectric transducer, and f is the frequency of the generated wave signal. The speed $v_{pzt}$ is the same speed as that of the traveling intensity grating. The speed $v_{pzt}$ is also the speed in the equation $\delta\omega=2\pi V_g/c$, and thus the frequency shift, including the frequency shift associated with the peak of the energy gain between the interfering waves, is directly proportional to the voltage applied to the piezoelectric transducer and can be accurately determined from that voltage. The speed $v_{pzt}$ can be varied either by varying the frequency of the generated wave signal or by varying the maximum displacement of the piezoelectric transducer for a given frequency. In the case of a triangle wave signal driving the piezoelectric transducer, a frequency difference $\delta\omega$ can be separately determined for each voltage level applied to the piezoelectric transducer.

Figure 7:
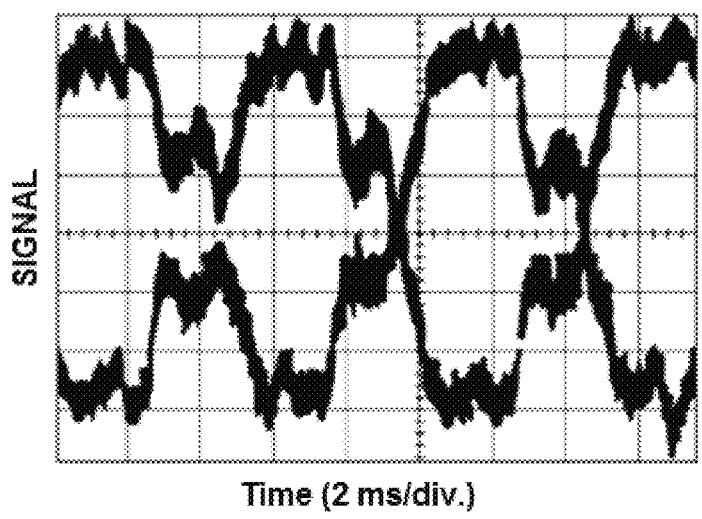
FIG. 7 shows the output of detectors illustrating an energy gain.
Figure 8:
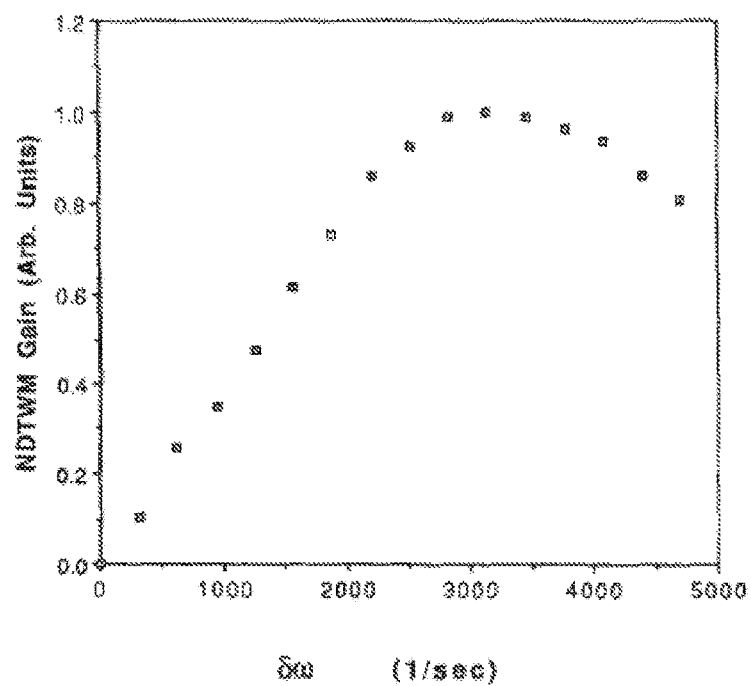
FIG. 8 illustrates a nondegenerate two-wave mixing gain signal as a function of Doppler shift, according to the present invention.

FIG. 6 shows a scope trace of the output from a detector that measures relative or normalized gain. The upper trace is proportion to the piezoelectric transducer displacement, and the lower trace is the nondegenerate two-wave mixing gain signal. FIG. 7 shows the output from detectors Det1 and Det2, illustrating that one wave gains energy at the expense of the other. FIG. 8 illustrates the nondegenerate two-wave mixing gain signal as a function of Doppler shift $\delta\omega$. The peak Doppler phase shift for data collected from a particular sample may be determined by performing a least-squares fit on the data. Further, the presence of macromolecules having different, distinct sizes in the colloidal suspension sample would result in a nondegenerate two-wave mixing gain curve having multiple, distinct frequency shift peaks.

Figure 9:
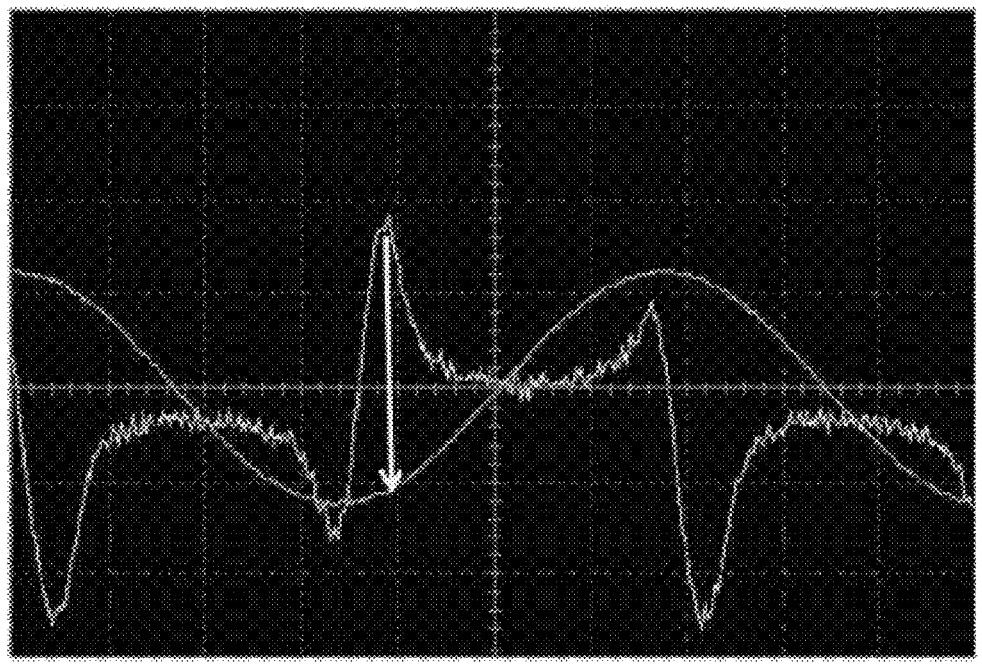
FIG. 9 shows a trace of displacement according to a sinusoidal wave signal and a nondegenerate two-wave mixing gain signal according to the present invention.

As shown in FIG. 9, in an alternate embodiment, the function generator that drives the piezoelectric transducer applies a voltage to the transducer in the form of a sinusoidal function (as shown). This results in the sinusoidal displacement of the piezoelectric transducer, such as $x=x_o \sin(2\pi f t)$. Accordingly, the instantaneous speed v of the transducer and its attached mirror driven is the derivative of the displacement function, namely $v=2\pi f x_o \cos(2\pi f t)$. As the piezoelectric transducer moves in accordance with a sinusoidal function, the speed also varies as a sinusoidal function between 0 and a maximum speed. Moreover, the frequency shift between the Doppler-shifted interfering waves is proportional of the movement of waves' sources relative to each other, in this case the speed of the mirror attached to the piezoelectric transducer. As shown in FIG. 9, if the speed of the piezoelectric transducer's movement varies from values greater than, equal to, and less than the speed at which the frequency shift $\delta\omega$ corresponds to the peak energy gain between the interfering waves, then the apparatus of the present invention can scan through all speeds that would generate a frequency shift $\delta\omega$ in the course of one period of the wave signal generated at the piezoelectric transducer to identify the frequency shift associated with the peak energy gain in that period (indicated by arrow in FIG. 9). Thus, the movement of the source of the Doppler-shifted waves, i.e. the piezoelectric transducer, in accordance with a sinusoidal function allows for extremely rapid scanning of values of $\delta\omega$ to determine the frequency shift at which the peak gain occurs, namely within a single period of the sinusoidal function.

Figure 10:
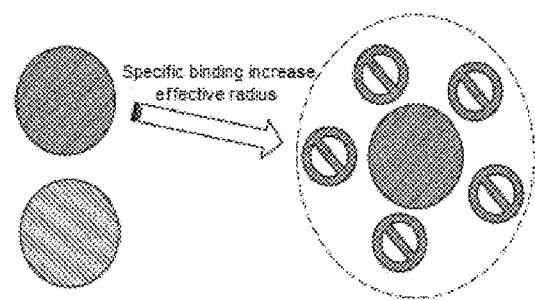
FIG. 10 illustrates specific binding of antibodies.
Figure 11:
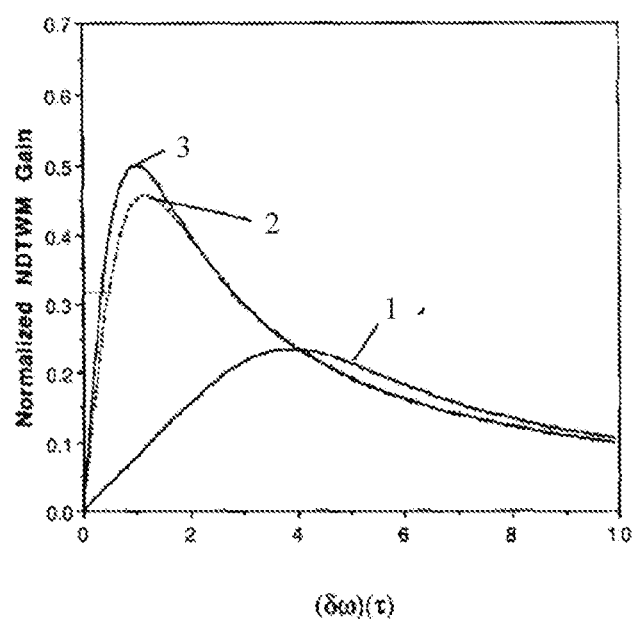
FIG. 11 illustrates a shift in peak frequency difference upon a specific binding reaction.

The identification or determination of a specific macromolecule or lysate can be accomplished by a specific binding reaction in the solution, e.g., biomolecules to which antibody binding has been applied. When a specific antibody is bound to a bioparticle, there is a change or shift in the radius and mass of the composite particle. As schematically illustrated in FIG. 10, specific binding of antibodies, for example, will increase the "size" of a specific protein and shift the nondegenerate two-wave mixing gain peak to a new position, which may be experimentally determined. In the example of FIG. 11, the peak may shift from position 1 to position 2 upon the application of a specific binding reaction. In this manner, a cluster of different molecules with otherwise similar nondegenerate two-wave mixing frequency peaks can be identified and differentiated using the technique of selecting binding. Further, a single type of molecule such as a protein can be analyzed to determine which one of a group of other molecules such as antibodies are able to bind to it.

In an alternative embodiment, the moving object in the interfering light wave grating includes a particle such as gold or other type of nanoparticle. In this case, the moiety or biomaterial of interest is selectively attached or bound to the particle. For example, gold or other types of nanoparticles may be functionalized to react and bind with proteins. Further, thiol linkers may be used to bind proteins with gold particles, and amines may be used to link with silica. The linkers can then attach selective antibodies that bind specific proteins.

The same methods of optical detection set forth above will apply to this alternative embodiment, and the frequency peak of the nondegenerate two-wave mixing gain signal is a direct function of the hydrodynamic radius of the bare or composite particle. The change in the frequency of the peak of the nondegenerate two-wave mixing gain signal is due to the size of the moiety, e.g., protein, attached to the particle, e.g., gold nanoparticle, which itself may be a sphere, rod etc. The change in the peak frequency of the nondegenerate two-wave mixing gain signal is indicative of the larger effective radius, which is used to determine the size of the moiety, e.g., protein. The radius of the particle will increase due to the selective binding of the specific protein, and the change in the nondegenerate two-wave mixing gain signal frequency peak relative to bare gold nanoparticles provides an estimate of the protein size according to the principles set forth above.

Figure 13:
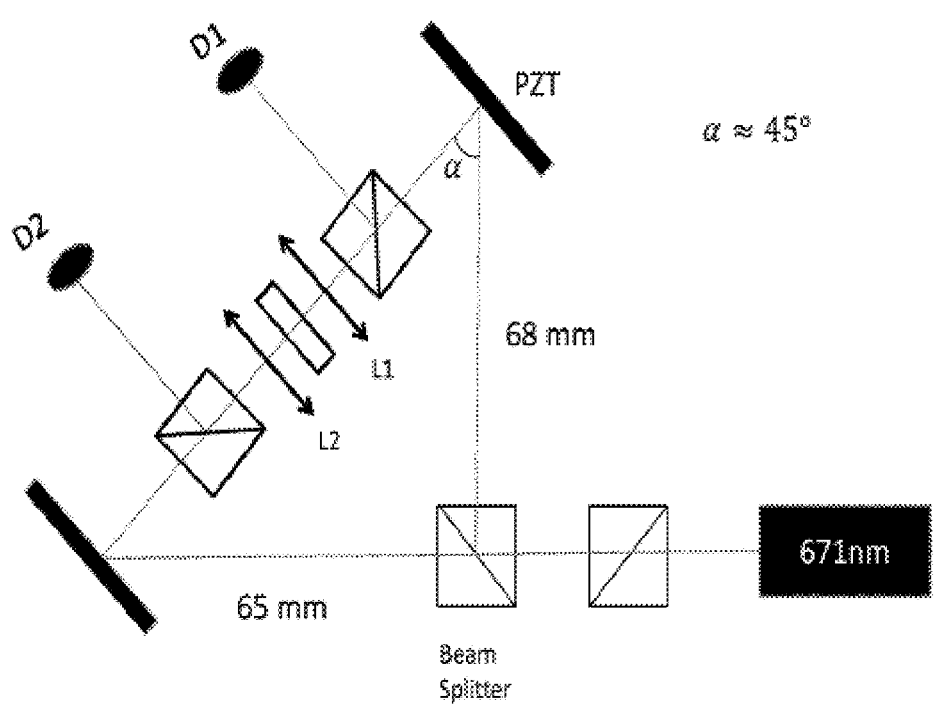
FIG. 13 illustrates an experimental arrangement for estimating the size of a moiety such as a protein according to the alternative embodiment of the present invention.
Figure 14:
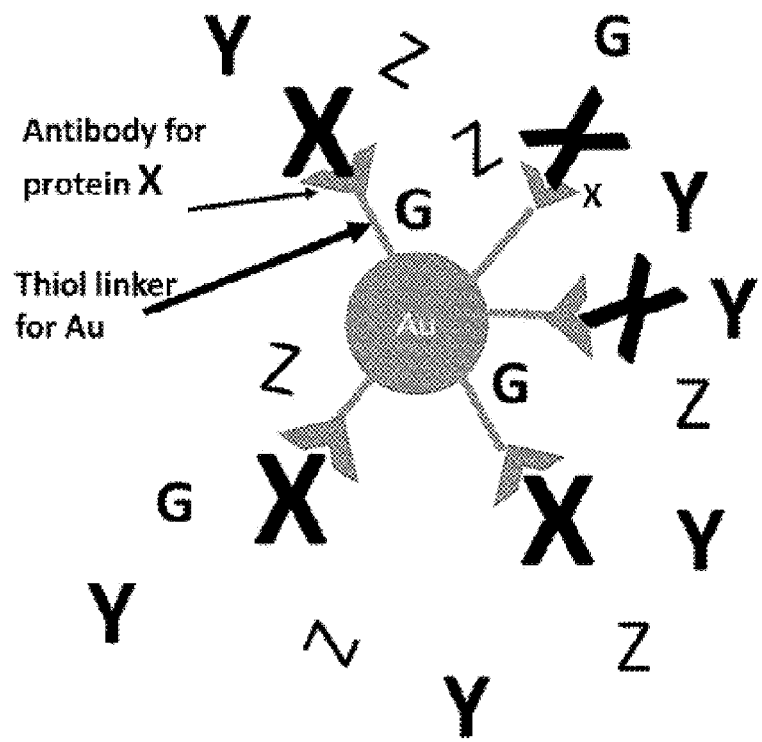
FIG. 14 illustrates the principles of selectivity and binding by which a gold particle may include linkers targeted to bind selectively to a protein according to the embodiment of FIG. 13.
Figure 15:
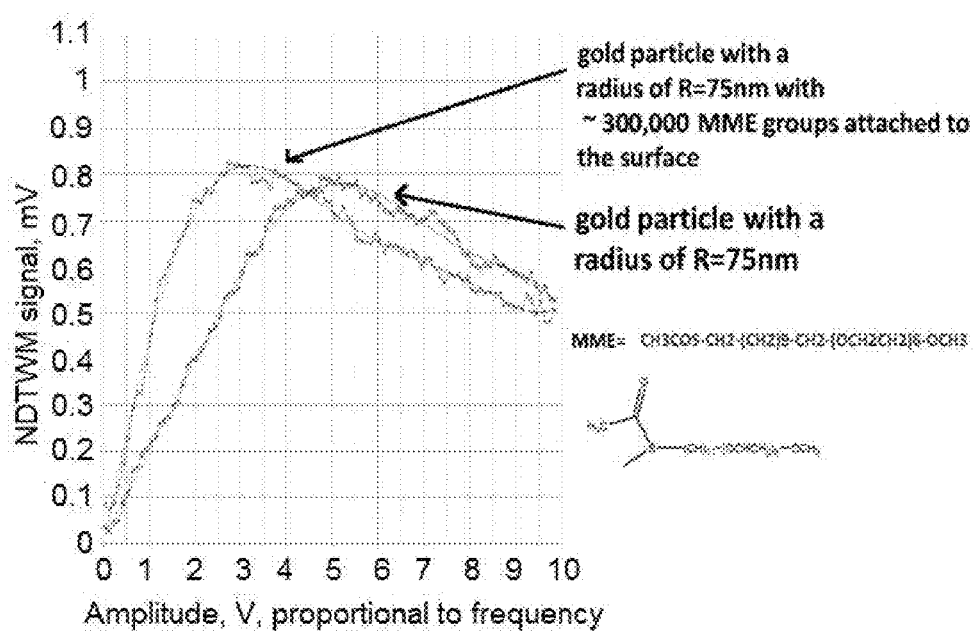
FIG. 15 is a graph that shows the shift in the peak frequency of the nondegenerate two-wave mixing gain signal according to the embodiment of FIG. 13.

FIG. 13 illustrates an experimental arrangement for estimating the size of a moiety such as a protein according to this embodiment of the present invention. FIG. 14 illustrates the principles of selectivity and binding by which a gold particle may include thiol linkers with antibodies targeted to bind selectively to a protein X, but not to proteins identified as Y and Z. FIG. 15 is a graph that shows the shift in the peak frequency of the nondegenerate two-wave mixing gain signal according to this embodiment of the invention. The right-most curve is the nondegenerate two-wave mixing gain signal for a bar gold particle having a radius of 75 nm, while the left-most curve is the nondegenerate two-waving mixing gain signal for a gold particle having a radius of 75 nm with thiol MME groups attached or linked to the surface of the particle. The left shift of the peak of the nondegenerate two-wave mixing gain signal curve results from the moieties attached to the gold particle increasing the effective radius of the composite particle.

Further, the eccentricity of an anisotropically-shaped molecule, such as a rod-shaped molecule, can be determined using the two-wave mixing technique described herein. In particular, the application of an external electric field to the specimen will affect the diffusion of anisotropic particles in the medium by orienting them such that particles' dipoles will align with the direction of the electric field. Changing the diffusion of the molecules in the medium will shift the frequency difference at which the peak gain occurs, since the peak frequency difference is proportional to the diffusion coefficient D of the particles in the medium. The electric field can be applied parallel or perpendicular to the direction of the movement of the optical interference grating, each orientation of the electric field having a different effect on the diffusion of the particles in the medium.

In addition to the determination of macroparticle "size" through the use of nondegenerate two-wave mixing, the hydrodynamic molecular shape of the particle can be estimated by applying two interfering waves, as previously described, with linear polarizations that are the same and that rotate together at an annular frequency that can be varied. When such interfering waves are applied to an anisotropically-shaped protein, for example a rod-shaped moiety, the optical field induces a torque through the anisotropy of the molecular polarizability tensor. For the limiting case of a very eccentric ellipse or rod, this tensor is dominated by the axial component along the rod's axis. In contrast, for a sphere there will be no torque and no orientation.

The torque applied to an anisotropically shaped molecule will drive molecular orientation, which is countered by rotational diffusion. For slow rotation rates, molecules will track the rotating polarization of the two optical fields, and for rapid rotation rates the molecules will not follow the rotating polarization and will remain in an isotropic thermal distribution, presenting an average polarizability for the two-wave mixing. When the molecules are able to track the rotation, the polarizability involved in the two-wave mixing energy exchange between the two waves will be enhanced above the rotationally averaged value. This means that once the optimal frequency difference is found at a fixed polarization and the effective "size," and hence mass, is determined, observing the roll-off of the signal as the polarization of the two beams is rotated at higher and higher frequencies will determine the anisotropy of the molecular moiety. This effect can be further utilized by attaching a specific binding antibody or molecular group that is rod-shaped to separate out clusters that may have the same peak frequency shift as well as rotational frequency roll off. In contrast, a spherical protein, for example, would not exhibit any change in the optimum two-wave mixing signal when the polarization of the two beams is rotated.

Figure 12:
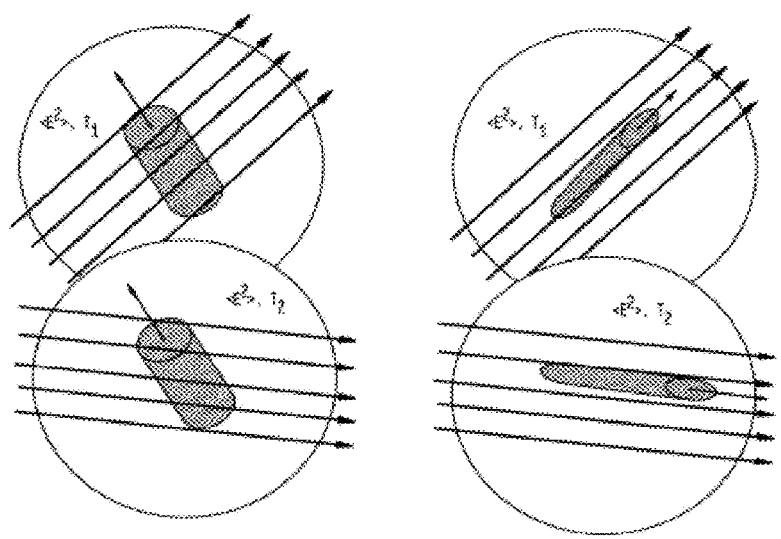
FIG. 12 illustrates the behavior of anisotropic molecules in a rotating polarization field.

FIG. 12 illustrates how two rod-shaped molecules will behave in a rotating polarization field. The molecule with a high aspect ratio (on the right) may track the rotation, while the molecule with a low aspect ratio (on the left) may not. In the case of a molecule with a low aspect ratio, two-wave mixing at the maximum $\delta\omega$ will not change as the frequency of the polarization rotation is varied.

The present invention may also be used to study the conformation or folding of large biomolecules such as proteins, e.g., titin, as described by Cieplak and Sulkowska (Institute of Physics, Polish Academy of Sciences, Warsaw, Poland). It has been found to be difficult to characterize the conformation of such large biomolecules using electrophoresis, due to the need to swell the pores of the electrophoretic gel in which they are analyzed. By varying the conditions of a protein sample such as titin, i.e., by varying the temperature and pH, the conformation or folding of the protein also changes, i.e., the protein unfolds or unwinds as it denatures. The change in the shape or hydrodynamic radius of such a large molecule, even in small volumes on the order of picoliters, can be examined using the method and apparatus of the present invention. By varying the temperature or pH of the specimen, the size and shape of a large molecule in solution such as a protein also changes, and the frequency shift $\delta\omega$ at which the peak gain occurs will also shift.

Figure 16:
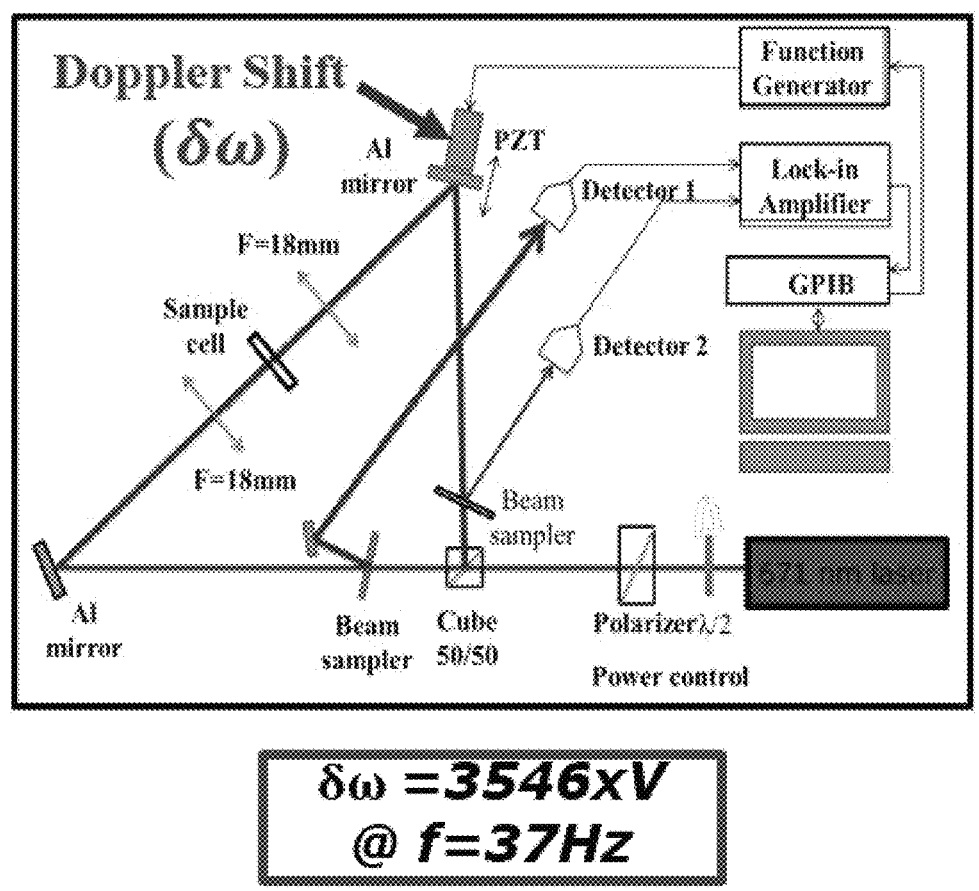
FIG. 16 illustrates an experimental setup for the present invention.

FIG. 16 illustrates an experimental setup of another embodiment of the present invention.

Figure 17:
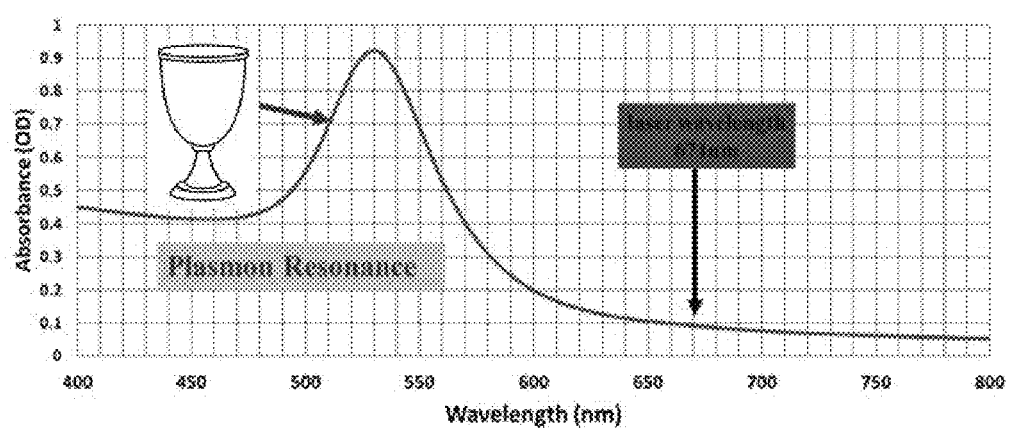
FIG. 17 illustrates an absorption spectrum for a 50 nanometer gold nanoparticle.

FIG. 17 illustrates an absorption spectrum for a 50 nanometer gold nanoparticle. It is understood that gold has a well-developed linker/corona library, and includes interactions with, e.g., thiols, polymers, and DNA.

Figure 18:
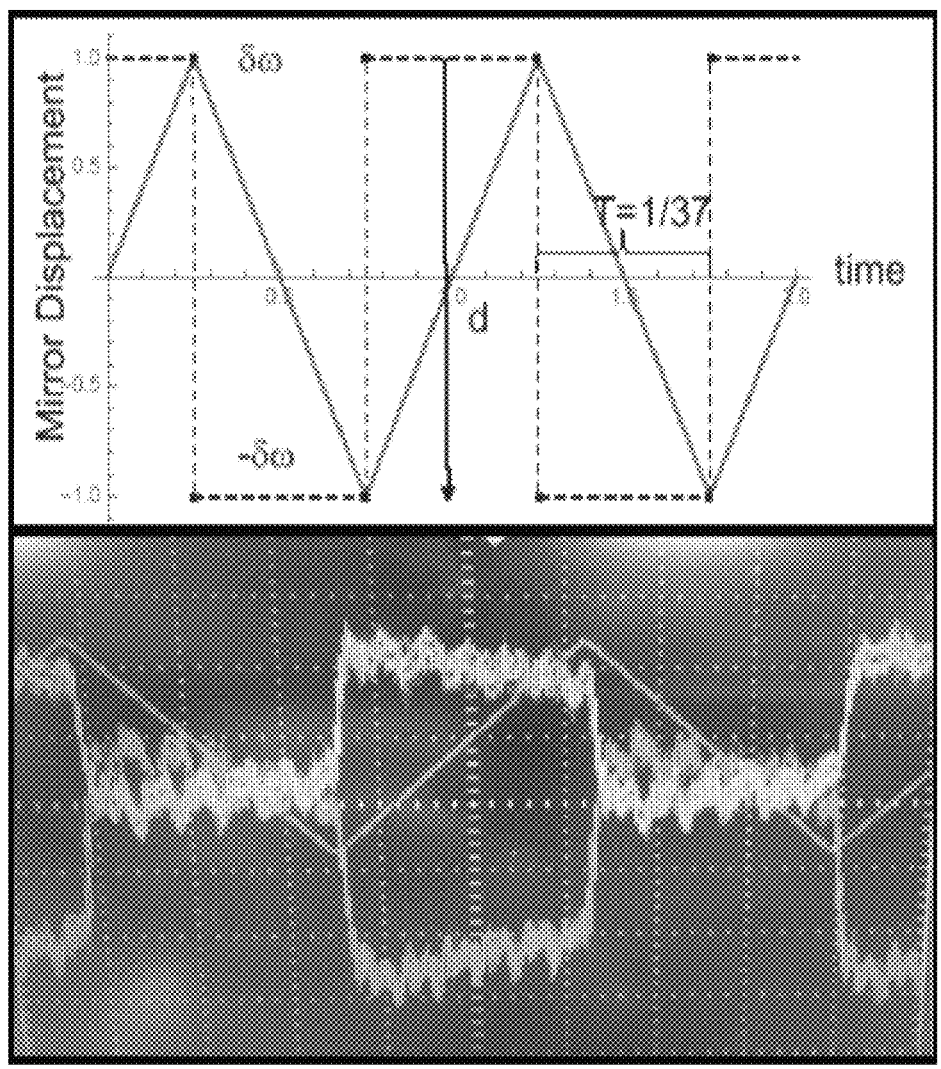
FIG. 18 illustrates Maxwell's equations and nonlinear material response in a colloidal system.

FIG. 18 illustrates Maxwell's equations and nonlinear material response in a colloidal system. When light intensity grating is out of phase with particle grating, the interfering waves exchange energy. This effect has its origin in the Doppler Effect and nonlinear optics. It is to be noted that the particles scattering light are moving at the precise speed to shift one frequency wave into the frequency of the other wave.

Figure 19:
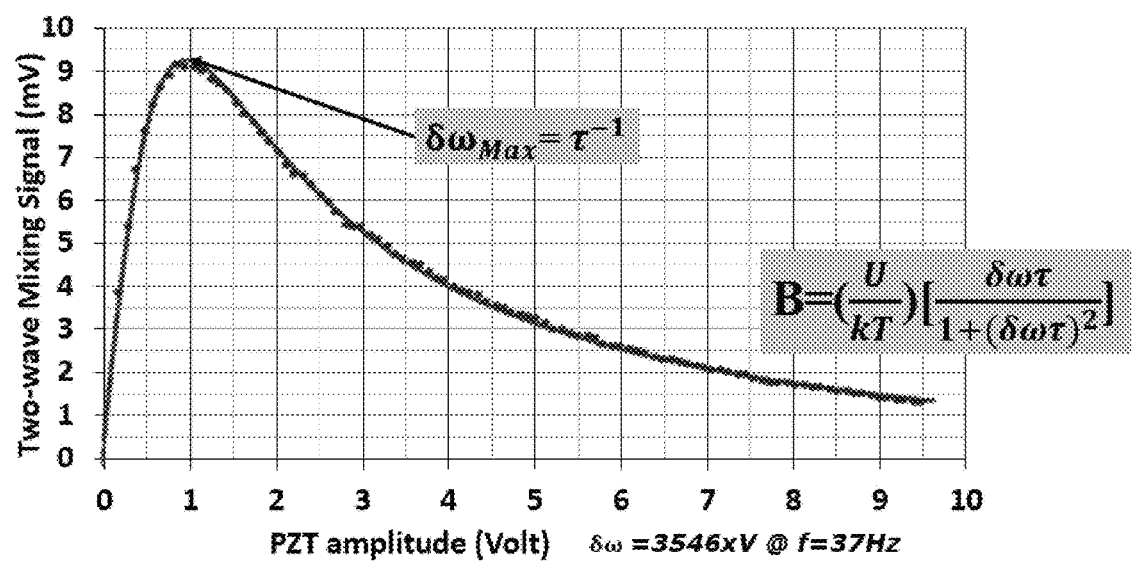
FIG. 19 illustrates a comparison of theoretical and actual two-wave mixing signals for monodispersed 50 nanometer gold nanoparticles over two orders of magnitude in concentration.

FIG. 19 illustrates a comparison of theoretical and actual two-wave mixing signals for monodispersed 50 nanometer gold nanoparticles over two orders of magnitude in concentration.

Figure 20:
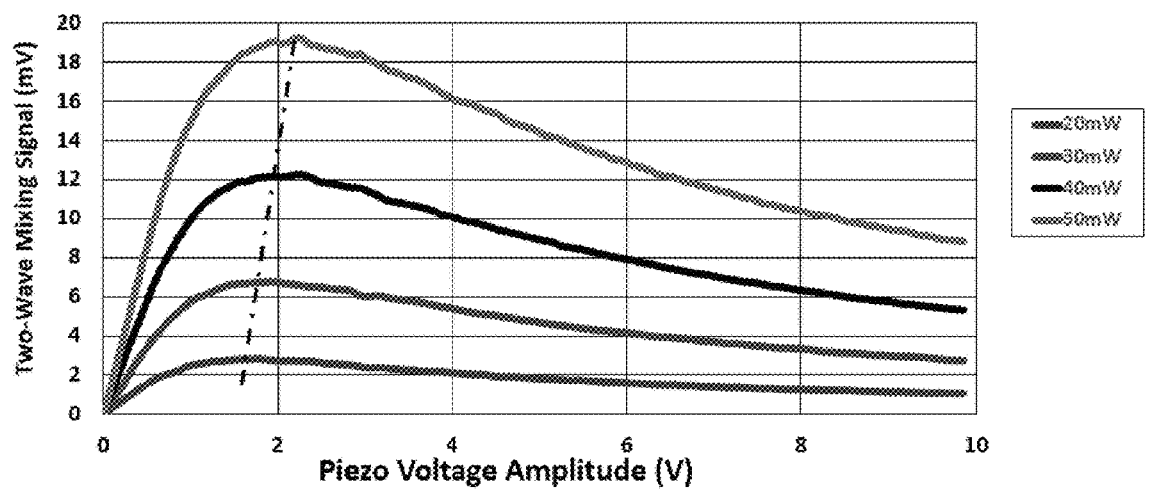
FIG. 20 illustrates laser power results in heating of the interaction region.

FIG. 20 illustrates laser power results in heating of the interaction region, where the heating depends solely on gold core particle size.

Figure 21:
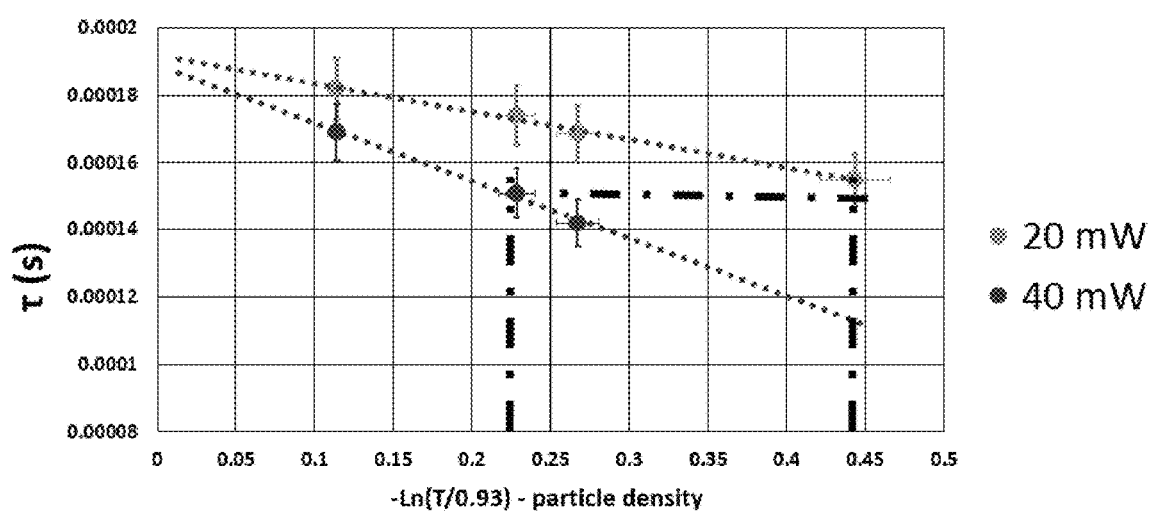
FIG. 21 illustrates a relationship between power and particle density.

FIG. 21 illustrates a relationship between power and particle density, specifically that power multiplied by particle density is equal to a constant representing the heat absorbed.

Figure 22:
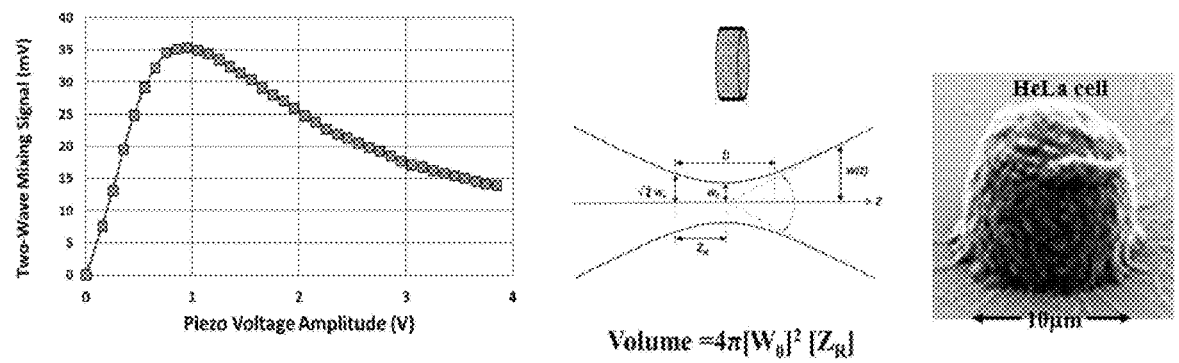
FIG. 22 illustrates the smallest measured samples of 12 microns thick resulting in characterization of 100 femtoliter volumes.

FIG. 22 illustrates that the smallest measured samples were 12 microns thick and resulted in characterization of 100 femtoliter volumes.

Figure 23:
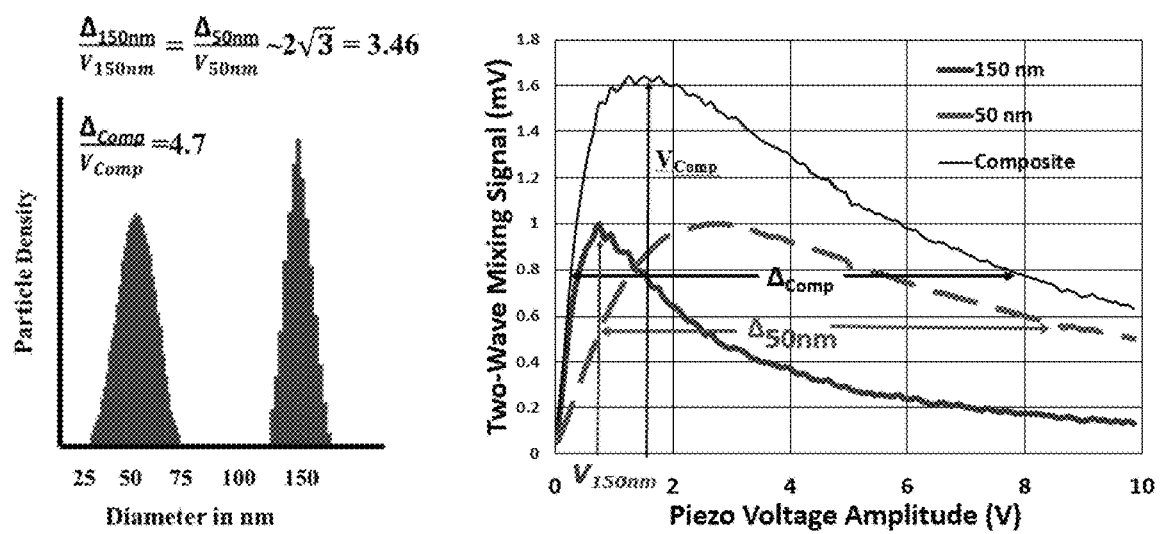
FIG. 23 illustrates a polydispersity analysis.
Figure 24:
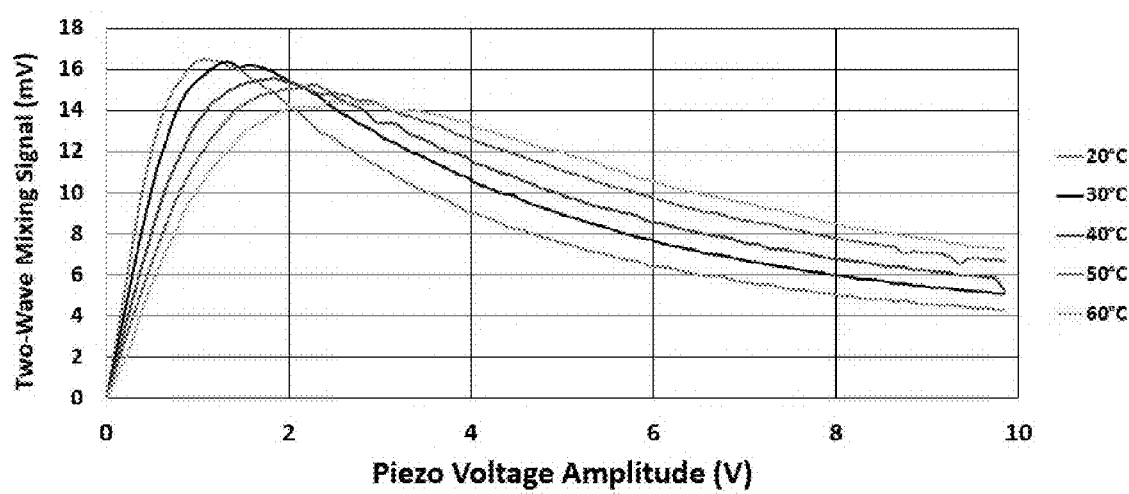
FIG. 24 illustrates a relationship between temperature and viscosity resolution.

FIG. 23 illustrates a polydispersity analysis, including a relationship between particle density and diameter (nanometer) as well as two-wave mixing signal (mV) and piezo voltage amplitude (V). FIG. 24 illustrates a relationship between temperature (° C.) and viscosity resolution. It is to be noted that the extracted viscosity for bare 50 nanometer gold nanoparticles matches the viscosity of water to within 1%.

Figure 25:
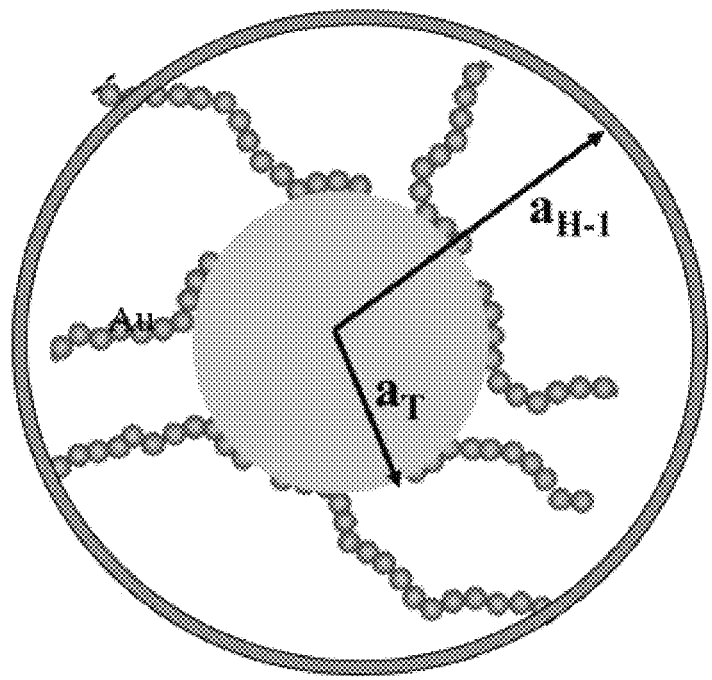
FIG. 25 illustrates a relationship between surface-bound moieties and core particles.
Figure 26:
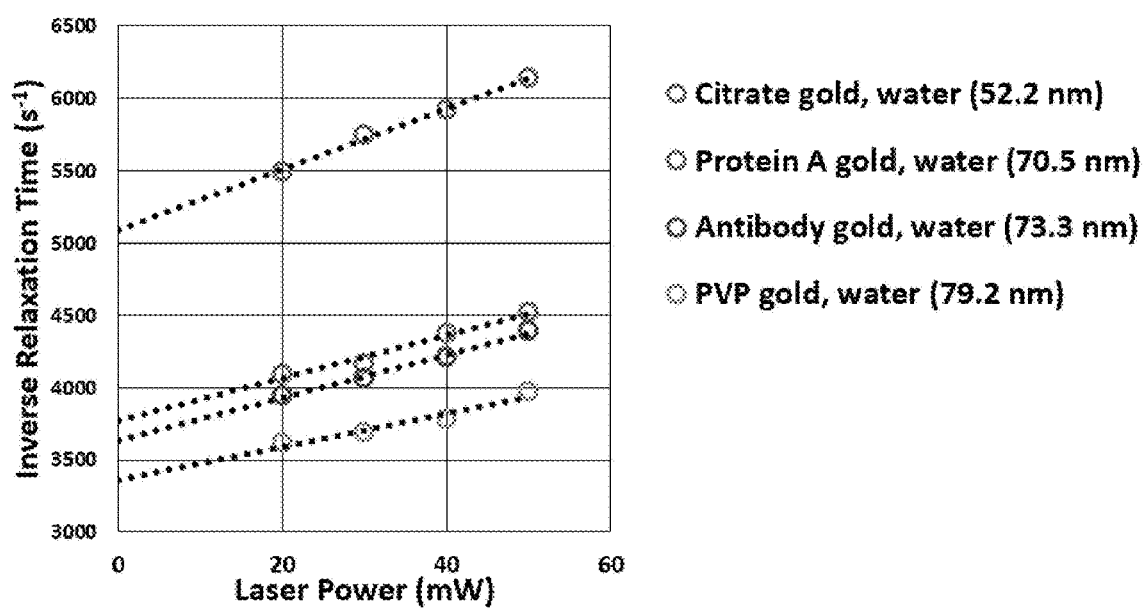
FIG. 26 illustrates several examples of surface-bound moieties on gold and their characteristics relating to inverse relaxation time and laser power.

FIG. 25 illustrates a relationship between surface-bound moieties and core particles, where ax represents the hydrodynamic radius, $a_{H-1}$ represents the radius of the surface-bound moiety and core particle, and $a_T$ represents the radius of the core particle, which has been measured by transmission electron microscopy (TEM). The TEM-measured radius of gold is 25 nanometers. FIG. 26 illustrates several examples of surface-bound moieties on gold and their characteristics relating to inverse relaxation time and laser power. The selected moieties include citrate, Protein-A, antibody, and polyvinylpyrrolidone (PVP).

Figure 27:
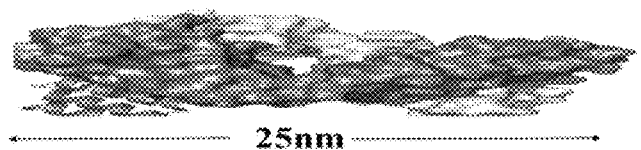
FIG. 27 illustrates Protein-A binding geometry to the surface of a 50 nanometer gold nanoparticle.
Figure 27:
Figure 27:
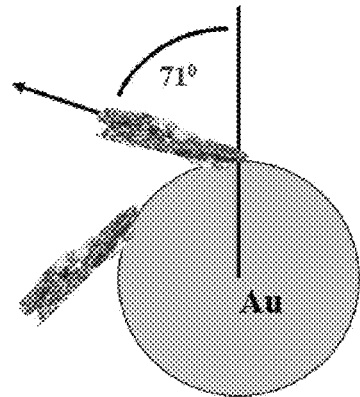
Figure 28:
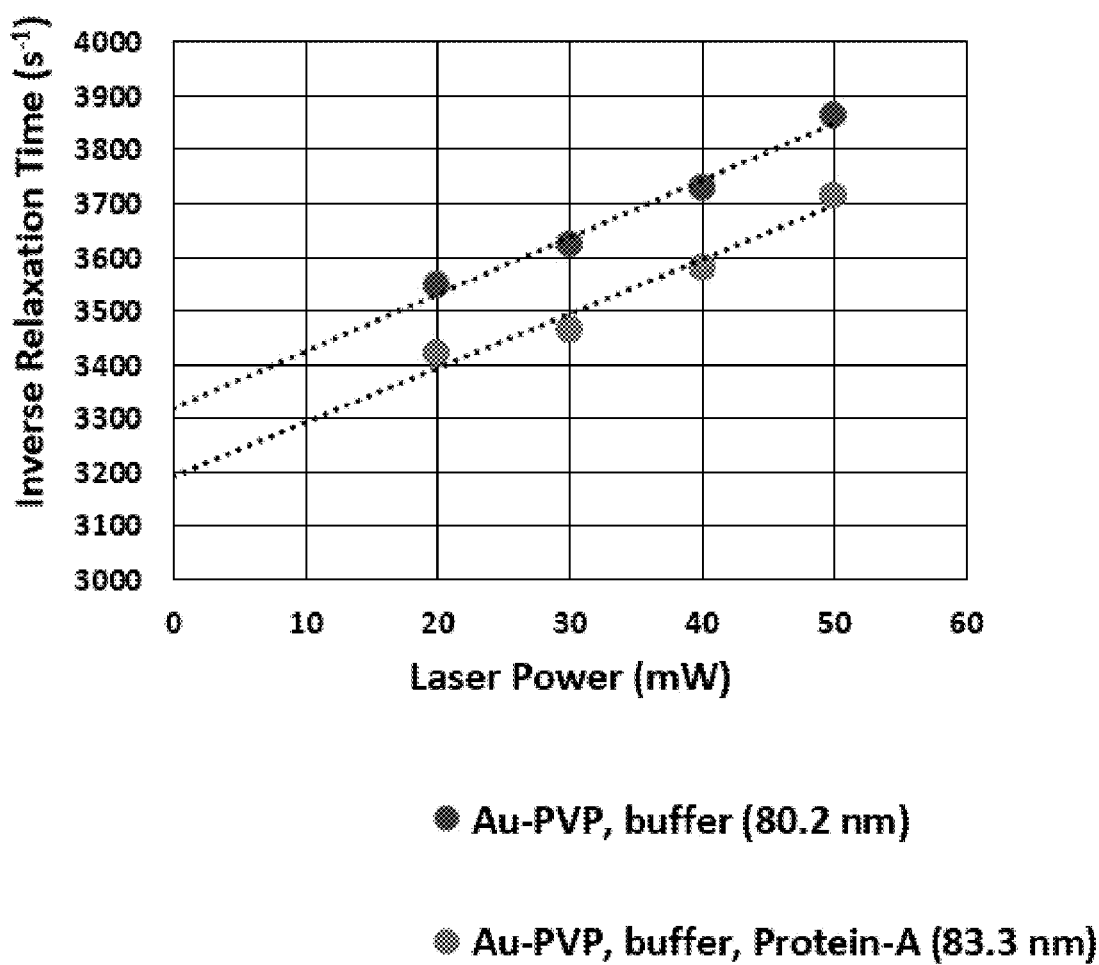
FIG. 28 illustrates Protein-A orientation on polyvinylpyrrolidone (PVP)-coated gold.
Figure 29:
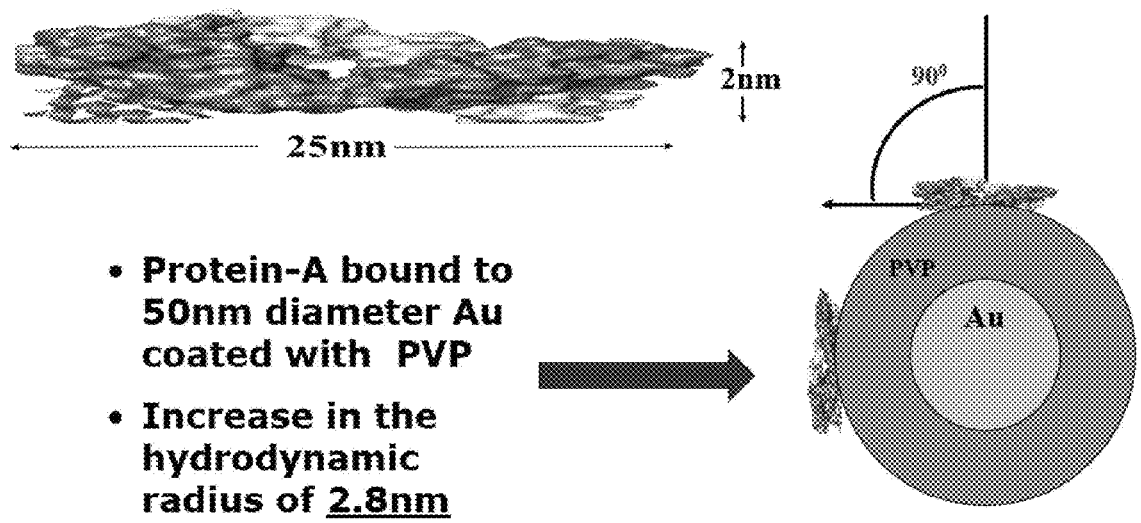
FIG. 29 illustrates Protein-A binding geometry to the surface of a PVP-coated 50 nanometer gold nanoparticle.

FIG. 27 illustrates the geometry of Protein-A binding to the surface of a 50 nanometer gold nanoparticle. Protein-A has a length of approximately 25 nanometers. When bound to the gold nanoparticle, Protein-A is bound at an angle of approximately 71° to the nanoparticle surface. Therefore, with the binding of Protein-A, the hydrodynamic radius is increased 8.3 nanometers. FIG. 28 illustrates Protein-A orientation on polyvinylpyrrolidone (PVP)-coated gold, specifically in relation to inverse relaxation time and laser power. Accordingly, Protein-A adds 1.5 nanometers to the surface of PVP. FIG. 29 illustrates the geometry of Protein-A binding to the surface of a PVP-coated 50 nanometer gold nanoparticle. Protein-A has a length of approximately 25 nanometers, and a height of approximately 2 nanometers. When bound to the gold nanoparticle coated with PVP, Protein-A is bound at an angle of approximately 90° to the coated nanoparticle surface. Therefore, with the binding of Protein-A, the hydrodynamic radius is increased 2.8 nanometers.

Figure 30:
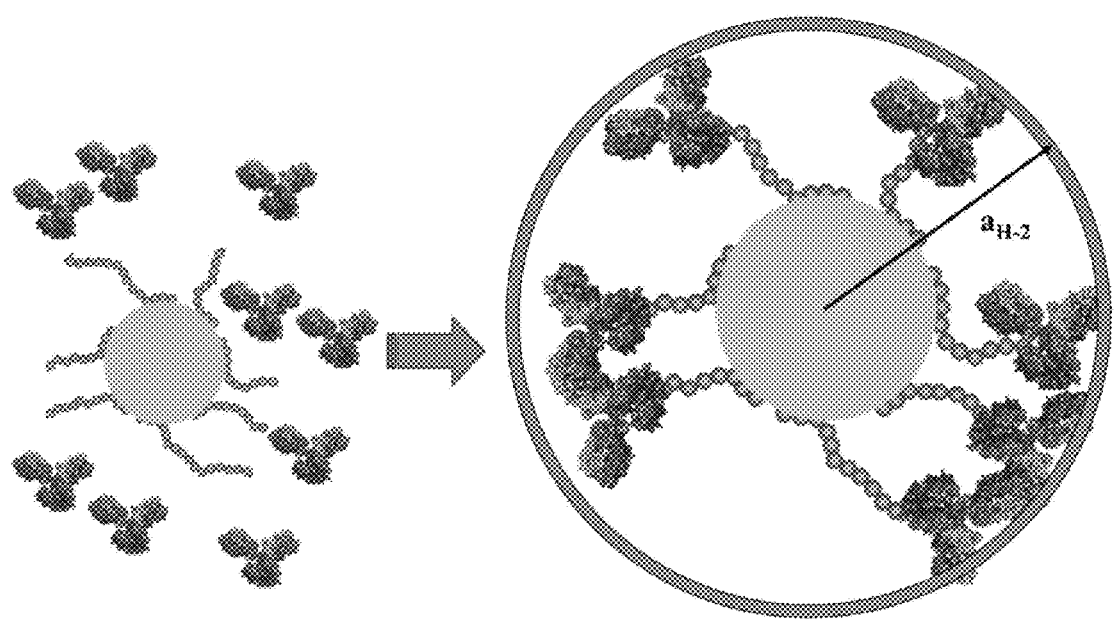
FIG. 30 illustrates a relationship between surface-bound moieties and core particles in reaction binding assays.

FIG. 30 illustrates a relationship between surface-bound moieties and core particles in reaction binding assays, where $a_{H-2}$ represents the radius of the surface-bound moieties and core particle.

Figure 31:
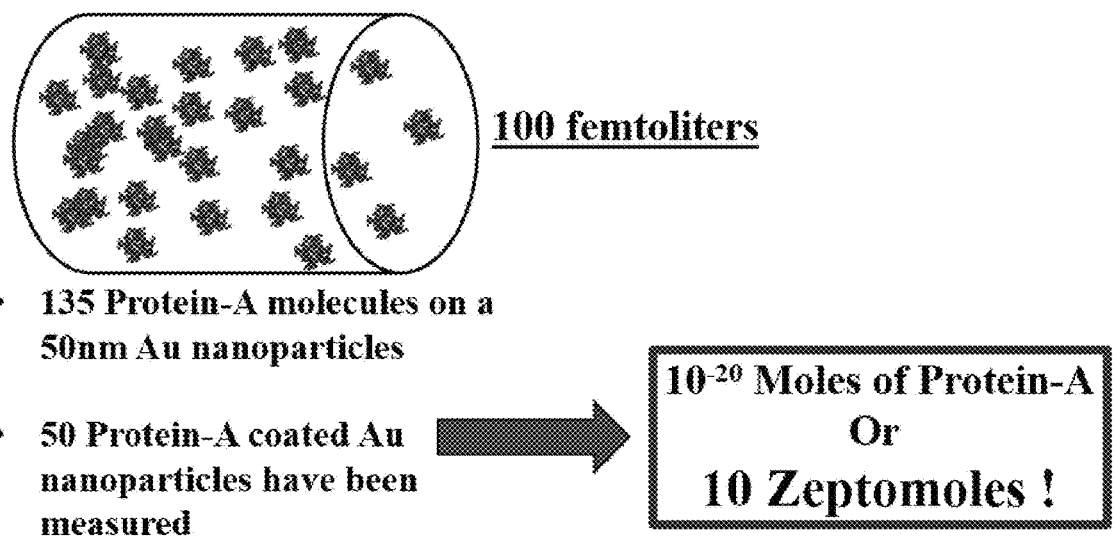
FIG. 31 illustrates an aspect of zeptomole sensitivity binding assays of Protein-A-bound 50 nanometer gold nanoparticles.

FIG. 31 illustrates an aspect of zeptomole sensitivity binding assays of Protein-A-bound 50 nanometer gold nanoparticles.

Figure 32:
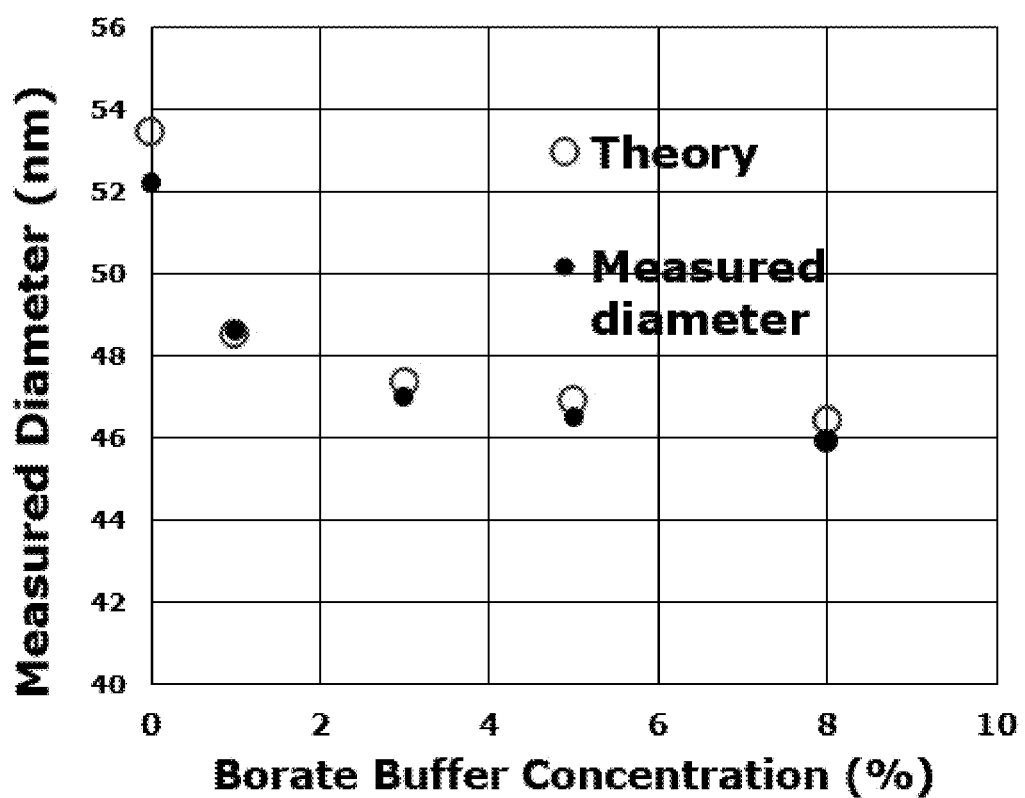
FIG. 32 illustrates determination of zeta potential in the absence of an electric field for citrate gold.

FIG. 32 illustrates determination of zeta potential in the absence of an electric field for citrate gold, as a relationship between measured diameter (nm) and borate buffer concentration (%). The employed model is based on equating screened potential at a given radius to $k_BT$. The zeta potential is fit to 35 mV.

Figure 33:
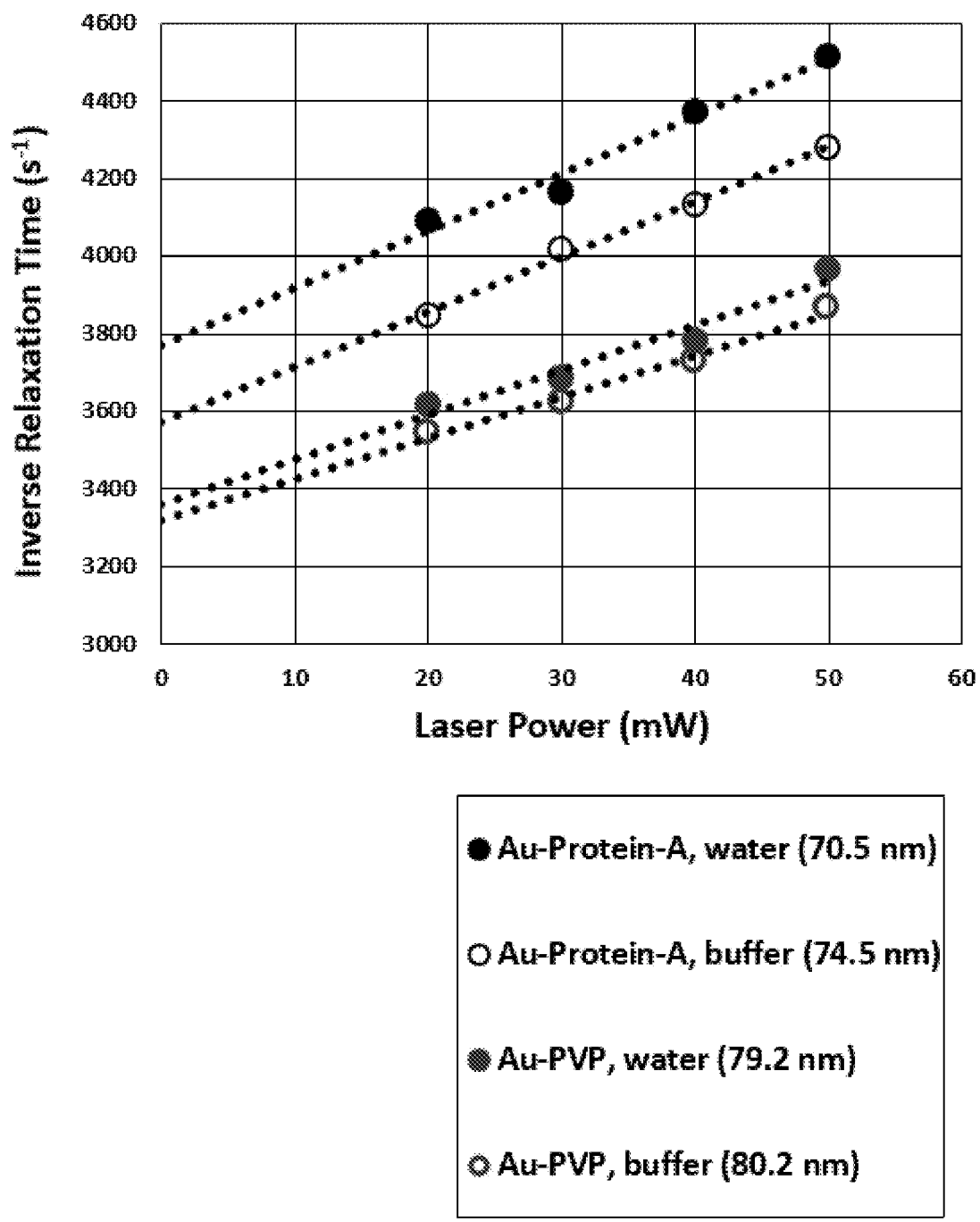
FIG. 33 illustrates ionic strength effects on protein and polymer surface conformation.

FIG. 33 illustrates ionic strength effects on protein and polymer surface conformation, as a relationship between inverse relaxation time and laser power. The selected protein is Protein-A, the selected polymer is PVP, and the core particle is gold nanoparticle. The environment may be water or buffer. In an electrolytic environment, Protein-A becomes more normal to the surface of the gold nanoparticle and PVP swells.

Figure 34:
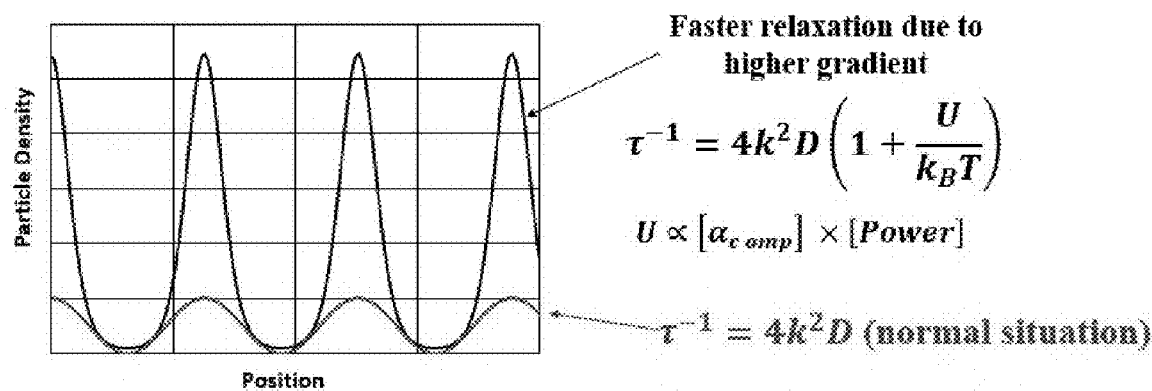
FIG. 34 illustrates an aspect of measuring surface moiety polarizability.
Figure 35:
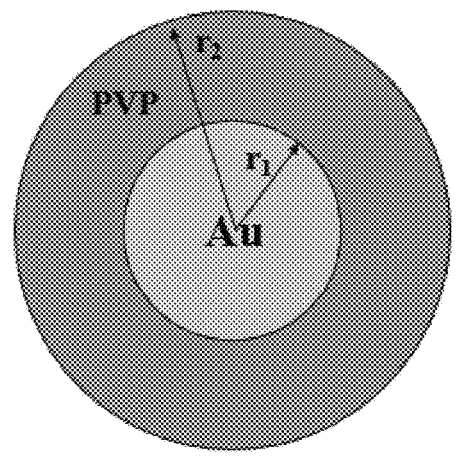
FIG. 35 illustrates a relationship regarding the polarizability of a gold nanoparticle-moiety system.
Figure 36:
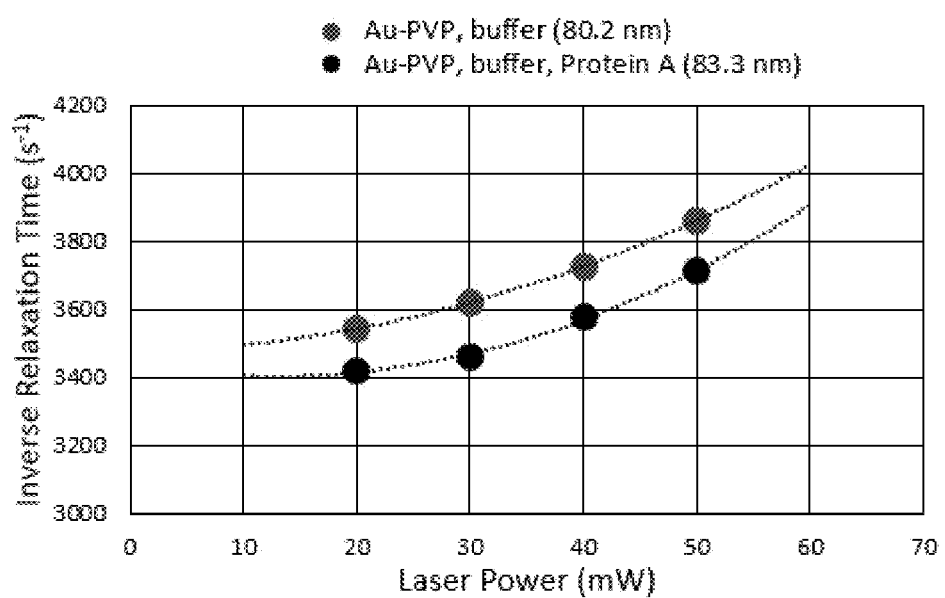
FIG. 36 illustrates an aspect of the polarizability of PVP-coated gold nanoparticles with and without bound Protein-A.

FIG. 34 illustrates an aspect of measuring surface moiety polarizability. At higher optical intensities and thicker attached moiety shells, the effect of the optical forces is strong enough to create non-sinusoidal gratings, which in turn relax at a faster rate due to a sharper Fick's Law gradient. FIG. 35 illustrates a relationship regarding the polarizability of a gold nanoparticle-moiety system. All of the coated gold nanoparticles are composite structures having a composite polarizability determined by the core-shell optical geometry and dielectric properties. FIG. 36 illustrates an aspect of the polarizability of PVP-coated gold nanoparticles with and without bound Protein-A, as a relationship between inverse relaxation time and laser power. The PVP-coated gold nanoparticles were shown to have a 15 nanometer shell thickness. Examination of the inverse relaxation time-laser power relationship shows that at higher powers, the straight line behavior of this relationship becomes quadratic. Moreover, inversion of the non-sinusoidal grating model predicts a dielectric constant for PVP of 2.5. This constant is in reasonable agreement with the index of refraction, which is 1.6.

Figure 37:
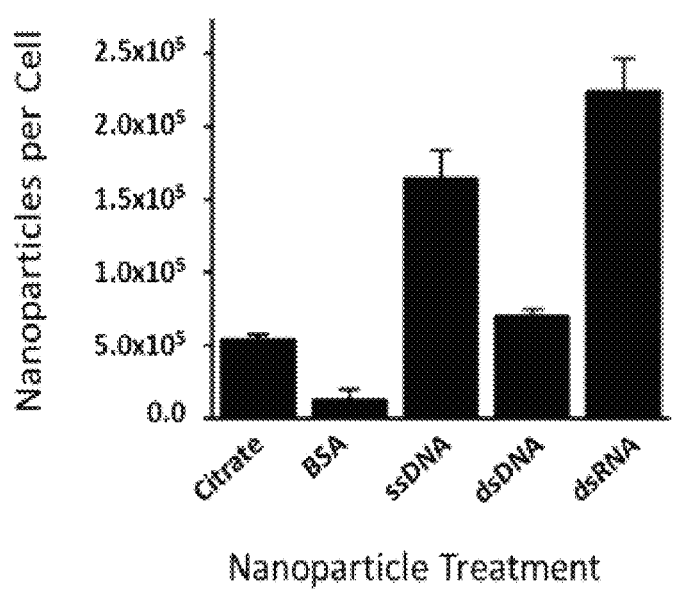
FIG. 37 illustrates a relationship between inter-cell viscosity and disease.

FIG. 37 illustrates a relationship between inter-cell viscosity and disease, specifically as a relationship between the number of nanoparticles per cell and certain nanoparticle treatments. It has been noted that cell viscosity research improves knowledge of cancer cells. See Kalwarczyk et al., "Comparative Analysis of Viscosity of Complex Liquids and Cytoplasm of Mammalian Cells at the Nanoscale," Nano Letters 11(5):2157-63 (2011).

Figure 38:
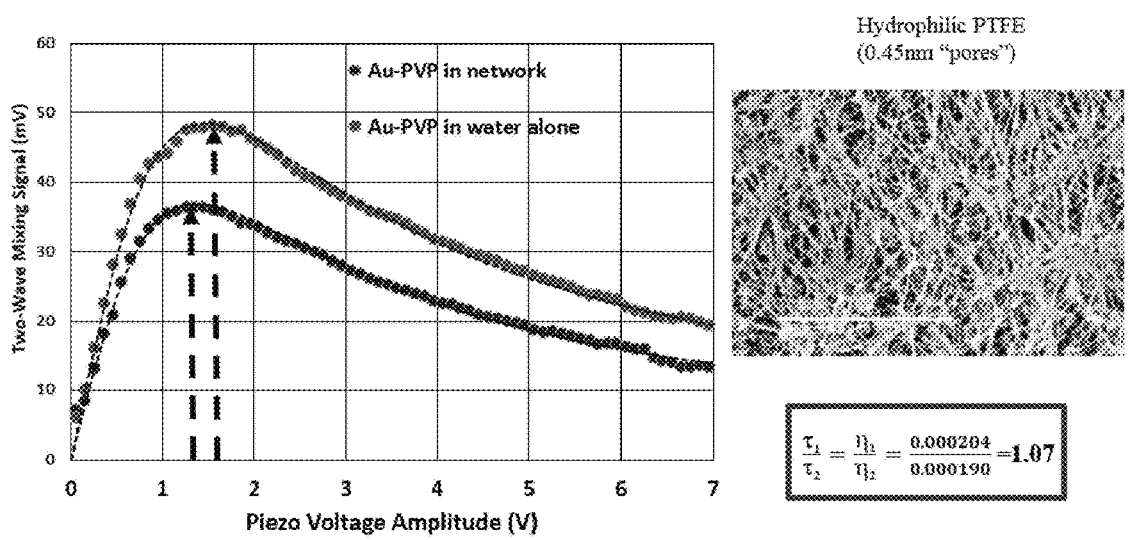
FIG. 38 illustrates an aspect of diffusion of PVP-coated gold nanoparticles in network.
Figure 39:
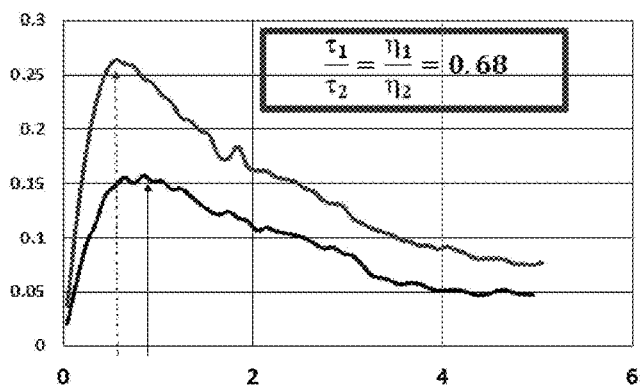
FIG. 39 illustrates another aspect of diffusion of PVP-coated gold nanoparticles in network.
Figure 39:
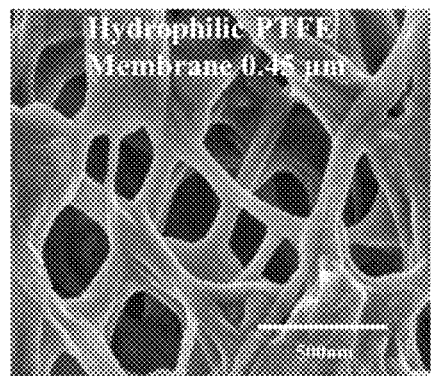

FIG. 38 illustrates an aspect of diffusion of PVP-coated gold nanoparticles in network, specifically as a relationship between two-wave mixing signal (mV) and piezo voltage amplitude (V) for PVP-coated gold nanoparticles in water alone and in network. FIG. 39 similarly illustrates an aspect of diffusion of PVP-coated gold nanoparticles in network.

Figure 40:
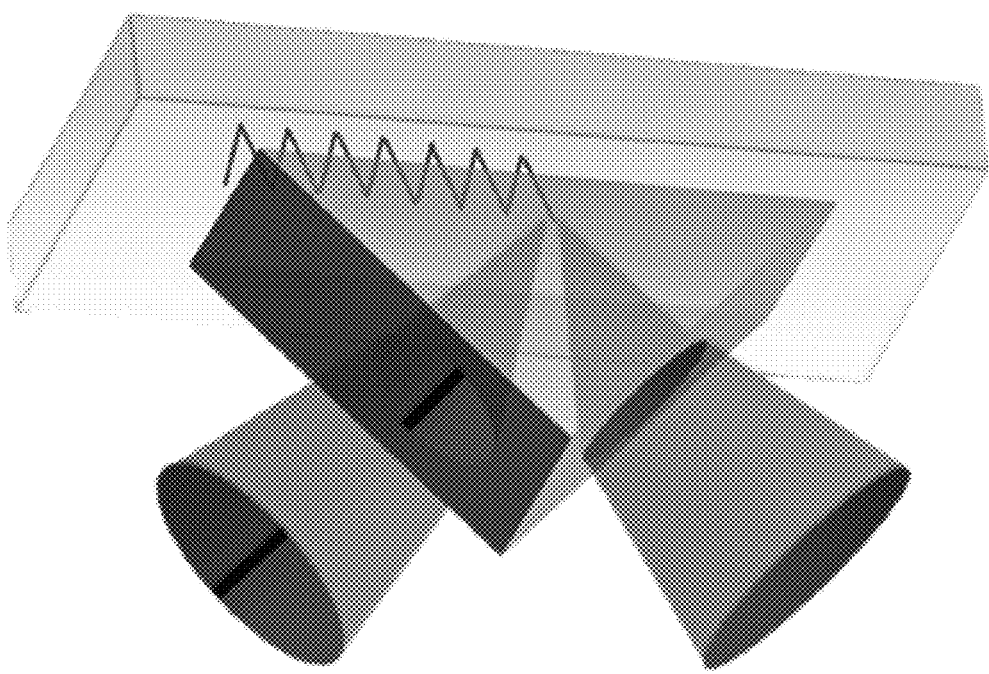
FIG. 40 illustrates cell coupling via a moving grating in an evanescent field of a prism.

FIG. 40 illustrates cell coupling via a moving grating in an evanescent field of a prism. The upper rectangular prism is indicative of a cell culture with intracellular gold nanoparticles, or skin or in vivo tissue with cells containing nanoparticles. Acceptable signal levels may be achieved through the use of nanoparticles in the range of $10^3$ to $10^4$ in 50 micron cell sizes.

The embodiments and examples above are illustrative, and many variations can be introduced to them without departing from the spirit of the disclosure or from the scope of the invention. For example, elements and/or features of different illustrative and exemplary embodiments herein may be combined with each other and/or substituted with each other within the scope of this disclosure. Therefore, it is intended that the invention not be limited to the particular embodiments disclosed, but that the invention will include all embodiments falling within the scope of the claims. For a better understanding of the invention, its operating advantages and the specific objects attained by its uses, reference should be had to the accompanying drawings and descriptive matter, in which there is illustrated a preferred embodiment of the invention.

What is claimed is:

1. A method for determining a radius of elements suspended in a medium, comprising:
binding the elements to nanoparticles to form bound element-nanoparticle aggregates;
superposing first and second frequency-shifted optical waves having a variable frequency shift between them in the medium such that there is a gain in energy of the first optical wave with respect to the second optical wave;
varying the frequency shift and measuring the gain while varying the frequency shift to determine the value of the frequency shift at which there is a peak in the gain;
determining the radius of the bound element-nanoparticle aggregates based on the value of the frequency shift at which there is a peak in the gain; and
determining the radius of the elements based on the radius of the bound element-nanoparticle aggregates.

2. The method of claim 1 wherein the first and second optical waves have low intensities.

3. The method of claim 1 wherein the radius of the bound element-nanoparticle aggregates is a hydrodynamic radius that is inversely related to the value of the frequency shift at which there is a peak in the gain.

4. The method of claim 1 wherein the elements are bioparticles.

5. The method of claim 4 wherein the bioparticles are proteins, antibodies, DNA strands, red blood cells, semen, or molecular or biological moieties.

6. The method of claim 1 wherein the nanoparticles are gold nanoparticles.

7. The method of claim 1 wherein the nanoparticles are coated nanoparticles.

8. The method of claim 7 wherein the coating of the coated nanoparticles comprises polyvinylpyrrolidone.

9. The method of claim 1 wherein the elements are bound to the nanoparticles via one or more linkers.

10. The method of claim 9 wherein the one or more linkers are one or more of thiols, amines, antibodies, and proteins.

11. The method of claim 1 wherein the phase shift varies from about 10 Hz to 10 MHz.

12. The method of claim 1 further comprising varying the conditions of the medium to analyze a conformation of the bound element-nanoparticle aggregates.

13. The method of claim 12 wherein the conditions varied are temperature or pH or both.

14. The method of claim 1 wherein the optical waves are light beams.

15. The method of claim 1 wherein the optical waves are laser beams.

16. The method of claim 1 wherein the first and second optical waves are substantially not absorbed by the bound element-nanoparticle aggregates or the medium.

17. The method of claim 1 wherein the bound element-nanoparticle aggregates are anisotropically shaped and the first and second optical waves have a linear polarization, and further comprising
rotating the linear polarization of the first and second optical waves at an annular frequency and varying the annular frequency to induce a torque on the bound element-nanoparticle aggregates to determine the anisotropy of the bound element-nanoparticle aggregates.

18. The method of claim 17 wherein determining the anisotropy of the bound element-nanoparticle aggregates provides an indication of the hydrodynamic molecular shape of the bound element-nanoparticle aggregates.

19. The method of claim 1 wherein the bound element-nanoparticle aggregates are anisotropically shaped, and further comprising
applying an electric field to the medium to align the bound element-nanoparticle aggregates in a direction.

20. The method of claim 1 wherein the elements are selectively bound to the nanoparticles.

21. The method of claim 1 wherein determining the radius of the elements based on the radius of the bound element-nanoparticle aggregates comprises subtracting, from a value of the radius of the bound element-nanoparticle aggregates, a value of the radius of the nanoparticles.

22. The method of claim 21 wherein the value of the radius of the nanoparticles is determined from measuring bare nanoparticles or by electron microscopy.

23. The method of claim 1 wherein the frequency-shifted optical waves are Doppler-shifted optical waves.

24. The method of claim 23 wherein the Doppler-shifted optical waves are produced by a moving reflective element or a moving mirror.

25. A method for determining a surface orientation of elements bound to nanoparticles in a medium, comprising:
binding the elements to the nanoparticles to form bound element-nanoparticle aggregates;
superposing first and second frequency-shifted optical waves having a variable frequency shift between them in the medium such that there is a gain in energy of the first optical wave with respect to the second optical wave;
varying the frequency shift and measuring the gain while varying the frequency shift to determine the value of the frequency shift at which there is a peak in the gain;
determining the radius of the bound element-nanoparticle aggregates based on the value of the frequency shift at which there is a peak in the gain; and
determining the surface orientation of the elements based on the radius of the bound element-nanoparticle aggregates.

26. The method of claim 25 wherein determining the surface orientation of the elements based on the radius of the bound element-nanoparticle aggregates comprises subtracting, from a value of the radius of the bound element-nanoparticle aggregates, a value of a dimension of the nanoparticles.

27. The method of claim 26 wherein the value of the dimension of the nanoparticles is determined from measuring bare nanoparticles or by electron microscopy.

28. The method of claim 25 wherein an attachment angle of the elements to the nanoparticles is determined from the surface orientation of the elements.

29. A method for measuring amounts of elements bound to nanoparticles in a solution, comprising:
binding the elements to the nanoparticles to form bound element-nanoparticle aggregates;
superposing first and second frequency-shifted optical waves having a variable frequency shift between them in the solution such that there is a gain in energy of the first optical wave with respect to the second optical wave;
varying the frequency shift and measuring the gain while varying the frequency shift to determine the value of the frequency shift at which there is a peak in the gain; and assaying the solution to determine amounts of the bound element-nanoparticle aggregates in the solution based on the value of the frequency shift at which there is a peak in the gain.

30. A method for measuring a change in viscosity in a cell having a medium containing nanoparticles of known size, comprising:

superposing first and second frequency-shifted optical waves having a variable frequency shift between them in the cell medium such that there is a gain in energy of the first optical wave with respect to the second optical wave;

varying the frequency shift and measuring the gain while varying the frequency shift to determine the value of the frequency shift at which there is a peak in the gain; and determining a viscosity of the cell medium based on the value of the frequency shift at which there is a peak in the gain.

31. The method of claim 30 further comprising determining a disease state based on the viscosity of the cell medium.

32. A method for determining a radius of elements suspended in a medium, comprising:

binding the elements to nanoparticles to form bound element-nanoparticle aggregates;

superposing first and second optical waves having the same frequency in the medium and moving the medium at a velocity to produce an effective Doppler shift between the first and second optical waves such that there is a gain in energy;

varying the effective Doppler shift and measuring the gain while varying the effective Doppler shift to determine the value of the effective Doppler shift at which there is a peak in the gain;

determining the radius of the bound element-nanoparticle aggregates based on the value of the effective Doppler shift at which there is a peak in the gain; and determining the radius of the elements based on the radius of the bound element-nanoparticle aggregates.

* * * * *